United States Patent
Chancellor et al.

(10) Patent No.: US 10,859,579 B2
(45) Date of Patent: Dec. 8, 2020

(54) METHODS FOR DETECTING, DIAGNOSING AND TREATING ULCERATIVE INTERSTITIAL CYSTITIS

(71) Applicant: WILLIAM BEAUMONT HOSPITAL, Royal Oak, MI (US)

(72) Inventors: Michael B. Chancellor, Pittsburg, PA (US); Laura Lamb, Beverly Hills, MI (US); Joseph J. Janicki, McKees Rocks, PA (US)

(73) Assignee: WILLIAM BEAUMONT HOSPITAL, Royal Oak, MI (US)

( * ) Notice: Subject to any disclaimer, the term of this patent is extended or adjusted under 35 U.S.C. 154(b) by 0 days.

(21) Appl. No.: 16/089,227

(22) PCT Filed: Mar. 31, 2017

(86) PCT No.: PCT/US2017/025501
§ 371 (c)(1),
(2) Date: Sep. 27, 2018

(87) PCT Pub. No.: WO2017/173342
PCT Pub. Date: Oct. 5, 2017

(65) Prior Publication Data
US 2019/0107545 A1    Apr. 11, 2019

Related U.S. Application Data

(60) Provisional application No. 62/315,766, filed on Mar. 31, 2016, provisional application No. 62/421,521, filed on Nov. 14, 2016.

(51) Int. Cl.
| | | |
|---|---|---|
| *G01N 33/50* | (2006.01) | |
| *A61K 38/00* | (2006.01) | |
| *G06F 15/00* | (2006.01) | |
| *A61B 5/00* | (2006.01) | |
| *C12Q 1/00* | (2006.01) | |
| *G01N 33/68* | (2006.01) | |

(52) U.S. Cl.
CPC ..... *G01N 33/6869* (2013.01); *G01N 33/6863* (2013.01); *G01N 33/6893* (2013.01); *A61B 5/00* (2013.01); *A61K 38/00* (2013.01); *C12Q 1/00* (2013.01); *G01N 2333/522* (2013.01); *G01N 2333/5412* (2013.01); *G01N 2333/5421* (2013.01); *G01N 2800/34* (2013.01); *G01N 2800/348* (2013.01); *G01N 2800/52* (2013.01); *G06F 15/00* (2013.01)

(58) Field of Classification Search
None
See application file for complete search history.

(56) References Cited

U.S. PATENT DOCUMENTS

| | | | |
|---|---|---|---|
| 8,961,954 B2 | 2/2015 | Chancellor et al. | |
| 2006/0194738 A1* | 8/2006 | Fong | A61K 38/08 514/8.4 |
| 2010/0166739 A1* | 7/2010 | Chancellor | G01N 33/6869 424/130.1 |
| 2012/0021407 A1 | 1/2012 | Haj-Ahmad | |
| 2012/0177665 A1 | 7/2012 | Chacko | |

FOREIGN PATENT DOCUMENTS

| | | |
|---|---|---|
| WO | 2000028082 A1 | 11/1999 |
| WO | 2014078232 A1 | 5/2014 |

OTHER PUBLICATIONS

Tyagi et al. Urinary Chemokines as Noninvasive Predictors of Ulcerative Interstitial Cystitis. The Journal of Urology vol. 187, 2243-2248 (Jun. 2012). (Year: 2012).*
Katsouli et al. The role of the chemokine CXCL1 in epithelialization, inflammation and ageing. Experimental Dermatology, vol. 20, No. 2, pp. 166-167. Abstract No. P026, Feb. 2011). (Year: 2011).*
Price et al. (Evaluation of a urine biomarker and pain in healthy, recurrent urinary tract infections, and painful bladder syndrome patients. Female Pelvic Medicine and Reconstructive Surgery, vol. 18, No. 5, Supp. Suppl. 2, pp. S126. Abstract No. 62 (Sep.-Oct. 2012). (Year: 2012).*
Peters et al. (Are Ulcerative and Nonulcerative Interstitial Cystitis/Painful Bladder Syndrome 2 Distinct Diseases? A Study of Coexisting Conditions Urology 78: 301-308 (2011). (Year: 2011).*
Arcade et al. Biomarkers for interstitial cystitis/painful bladder syndrome. Womens Health (2016) 12(1), 87-90 (published online Dec. 23, 2015). (Year: 2016).*
Ercan et al. Stability of urine specimens stored with and without preservatives at room temperature and on ice prior to urinalysis. Clinical Biochemistry 48:919-922 (2015). (Year: 2015).*
Kouri et al. Preservation of Urine for Flow Cytometric and Visual Microscopic Testing. Clinical Chemistry 48:6:900-905 (2002). (Year: 2002).*

(Continued)

*Primary Examiner* — Elizabeth C. Kemmerer
*Assistant Examiner* — Regina M DeBerry
(74) *Attorney, Agent, or Firm* — Honigman LLP; Douglas H. Siegel; Jonathan P. O'Brien

(57) ABSTRACT

The present invention relates to methods for detecting, diagnosing and/or treating ulcerative interstitial cystitis (UIC) by detecting in a urine sample from a patient the levels of each of the proteins IL-6, IL-8 and GRO [also known as CXCL 1 (chemokine C-X-C motif ligand 1]. In some embodiments, the method also includes diagnosing the patient with UIC when each of the proteins IL-6, IL-8 and GRO in the urine sample is at a different level than a statistically validated threshold for the respective proteins. In some embodiments a companion diagnostic, e.g., a cystoscopy, is used in conjunction with the protein biomarker diagnostic. In some embodiments, once UIC is diagnosed, the patient is treated for the UIC.

27 Claims, 12 Drawing Sheets

Specification includes a Sequence Listing.

(56) References Cited

OTHER PUBLICATIONS

Nillen et al. The Use of Chlorhexidine/n-Propyl Gallate as a Urine Preservative. Clinical Laboratory Science; vol. 17, 3; p. 149-154 (2004). (Year: 2004).*

Lulu et al. Urimem, a membrane that can store urinary proteins simply and economically, makes the large-scale storage of clinical samples possible vol. 57 No. 3: 336-339 (Mar. 2014). (Year: 2014).*

Brunner, K. et al. Isothermal amplification in food analysis—a real alternative to conventional PCR. L&M Int. 2014;4:12-5.

Chancellor, M.B., et al. Lyme disease presenting as urinary retention. The Journal of urology. 1990;143(6):1223-4. PubMed PMID: 2342186.

Chancellor, M.B., et al. Lyme cystitis and neurogenic bladder dysfunction. Lancet. 1992;339(8803):1237-8. PubMed PMID: 1349976.

Chancellor, M.B., et al. Urinary dysfunction in Lyme disease. The Journal of urology. 1993;149(1):26-30. PubMed PMID: 8417211.

Doiron, R. Christopher, et al. "Clinical Phenotyping does Not Differentiate Hunner Lesion Subtype of Interstitial Cystitis/Bladder Pain Syndrome: A relook at the Role of Cystoscopy" J. Urol. 2016 vol. 196, 1136-1140.

Erickson, D.R., et al. "A comparison of multiple urine markers for interstitial cystitis" J. Urol. Jun. 2002; 167(6): pp. 2461-2469.

Francois, P., et al. Robustness of a loop-mediated isothermal amplification reaction for diagnostic applications. FEMS immunology and medical microbiology. 2011;62(1):41-8. doi: 10.1111/j.1574-695X.2011.00785.x. PubMed PMID: 21276085.

Gandasegui, J., et al. The Rapid-Heat LAMPellet Method: A Potential Diagnostic Method for Human Urogenital Schistosomiasis. PLoS neglected tropical diseases. 2015;9(7):e0003963. Epub Aug. 1, 2015. doi: 10.1371/journal.pntd.0003963. PubMed PMID: 26230990; PubMed Central PMCID: PMCPMC4521856.

Hirayama, T., et al. Detection of dengue virus genome in urine by real-time reverse transcriptase PCR: a laboratory diagnostic method useful after disappearance of the genome in serum. Journal of clinical microbiology. 2012;50 (6):2047-52. doi: 10.1128/JCM.06557-11. PubMed PMID: 22442323; PubMed Central PMCID: PMC3372171.

International Search Report and Written Opinion re PCT/US17/25501 dated Jul. 7, 2017.

Koizumi, N., et al. A new loop-mediated isothermal amplification method for rapid, simple, and sensitive detection of Leptospira spp. in urine. Journal of clinical microbiology. 2012;50(6):2072-4. doi: 10.1128/JCM.00481-12. PubMed PMID: 22422858; PubMed Central PMCID: PMC3372145.

Kuo, H.C., et al. Can Urinary Nerve Growth Factor Be a Biomarker for Overactive Bladder? Reviews in Urology. 2010;12(2-3):e69-e77. PubMed PMID: PMC2931284.

Kuo, H.C., et al. Promise of Urinary Nerve Growth Factor for Assessment of Overactive Bladder Syndrome. Lower urinary tract symptoms. 2011;3(1):2-9. doi: 10.1111/j.1757-5672.2011.00087.x. PubMed PMID: 26676344.

Kuo, H.C., et al. Urinary nerve growth factor is a better biomarker than detrusor wall thickness for the assessment of overactive bladder with incontinence. Neurourol Urodyn. 2010;29(3):482-487. doi: 10.1002/nau.20741. PubMed PMID: 19367641.

Kuo, H.C., et al. Urinary Nerve Growth Factor Levels in Urinary Tract Diseases With or Without Frequency Urgency Symptoms. Lower urinary tract symptoms. 2010;2(2):88-94. doi: 10.1111/j.1757-5672.2010.00065.x. PubMed PMID: 26676289.

Liu, H.T., et al. Urinary nerve growth factor levels are elevated in patients with detrusor overactivity and decreased in responders to detrusor botulinum toxin-A injection. Eur Urol. 2009;56(4):700-6. doi: 10.1016/j.eururo.2008.04.037. PubMed PMID: 18472208.

Liu, H.T., et al. Decrease of urinary nerve growth factor levels after antimuscarinic therapy in patients with overactive bladder. BJU Int. 2009;103(12):1668-72. doi: 10.1111/j.1464-410X.2009.08380.x. PubMed PMID: 19220267.

Liu, H.T., et al. Urinary nerve growth factor but not prostaglandin E2 increases in patients with interstitial cystitis/bladder pain syndrome and detrusor overactivity. BJU Int. 2010;106(11):1681-5. doi: 10.1111/j.1464-410X.2009.08851.x. PubMed PMID: 19751258.

Liu, H.T., et al. Urinary nerve growth factor level could be a biomarker in the differential diagnosis of mixed urinary incontinence in women. BJU Int. 2008;102(10):1440-4. doi: 10.1111/j.1464-410X.2008.07757.x. PubMed PMID: 18489524.

Liu, H.T., et al. Urinary nerve growth factor level is correlated with the severity of neurological impairment in patients with cerebrovascular accident. BJU Int. 2009;104(8):1158-62. doi: 10.1111/j.1464-410X.2009.08533.x. PubMed PMID: 19338537.

Liu, H.T., et al. Urinary nerve growth factor level is increased in patients with interstitial cystitis/bladder pain syndrome and decreased in responders to treatment. BJU International. 2009;104(10):1476-81. doi: 10.1111/j.1464-410X.2009.08675.x. PubMed PMID: 19522864.

Lotz, Martin, et al. "Interleukin-6 and Interstitial Cystitis," The Journal of Urology, vol. 152, 869-873 Sep. 1994.

Notomi, T., et al. Loop-mediated isothermal amplification of DNA. Nucleic acids research. 2000;28(12):E63. PubMed PMID: 10871386; PubMed Central PMCID: PMC102748.

Ogawa, T., et al. "CXCR3 Binding Chemokine and TNFSF14 Over Expression in Bladder Urothelium of Patients with Ulcerative Interstitial Cystitis" The Journal of Urology, 2010, vol. 183, No. 3, pp. 1206-1212; abstract.

Paduch, D.A. Viral lower urinary tract infections. Current urology reports. 2007;8(4):324-35. PubMed PMID: 18519018.

Patel, P., et al. Development of one-step quantitative reverse transcription PCR for the rapid detection of flaviviruses. Virology journal. 2013;10:58. doi: 10.1186/1743-422X-10-58. PubMed PMID: 23410000; PubMed Central PMCID: PMC3616844.

Peters, K.M., et al. "Preliminary study on urinary cytokine levels in interstitial cystitis: does intravesical bacilli Calmette-Guerin treat interstitial cystitis by altering the immune profile in the bladder?" Urology, 1999; 54(3):450-453.

Poon, L.L., et al. Detection of human influenza A viruses by loop-mediated isothermal amplification. Journal of clinical microbiology. 2005;43(1):427-30. Epub Jan. 7, 2005. doi: 10.1128/jcm.43.1.427-430.2005. PubMed PMID: 15635005; PubMed Central PMCID: PMCPMC540134.

Reyes, J.C., et al. Development of a loop-mediated isothermal amplification assay for detection of Trichomonas vaginalis. Diagnostic microbiology and infectious disease. 2014;79(3):337-41. doi: 10.1016/j.diagmicrobio.2014.03.016. PubMed PMID: 24792836.

Rivas, D.A., et al. Molecular marker for development of interstitial cystitis in rat model: isoactin gene expression. The Journal of urology. 1997;157(5):1937-40. PubMed PMID: 9112567.

Tomita, N. et al. Loop-mediated isothermal amplification (LAMP) of gene sequences and simple visual detection of products. Nature protocols. 2008;3(5):877-82. Epub May 3, 2008. doi: 10.1038/nprot.2008.57. PubMed PMID: 18451795.

Tyagi, P., et al. Association of inflammaging (inflammation+aging) with higher prevalence of OAB in elderly population. International urology and nephrology. 2014;46(5):871-7. doi: 10.1007/s11255-013-0621-x. PubMed PMID: 24323058.

Tyagi. Pradeep, et al. "Urinary Chemokines as Noninvasive Predictors of ulcerative Interstitial Cystitis" J Urol. Jun. 2012; 187(6): pp. 2243-2248.

Zhang, Chen-Ou, et al. "APF, HB-EGF, and EGF biomarkers in patients with ulcerative vs. non-ulcerative interstitial cystitis" BMC Urology 2005, 5:7, 7 pages.

* cited by examiner

```
def init_random_forest_clf(**kwargs):
    """
    Wrapper to construct a random forest classifier model.

Any keyword args provided to this function will overwrite the
    hardcoded default args below. The default args below are
    the result of optimizations to the IP4IC dataset, and are not
    the sklearn defaults (shown to the right as comments).
    """
    default_args = {
        'n_estimators':90,                          #default: 10
        'criterion':'gini',                         #default: 'gini'
        'max_features':'auto',                      #default: 'auto'
        'max_depth':None,                           #default: None
        'min_samples_split':2,                      #default: 2
        'min_samples_leaf':1,                       #default: 1
        'min_weight_fraction_leaf':0.,              #default: 0.
        'max_leaf_nodes':None,                      #default: None
        'bootstrap':True,                           #default: True
        'oob_score':True,                           #default: False
        'n_jobs':-1,                                #default: 1
        'random_state':42,                          #default: None
        'verbose':0,                                #default: 0
        'warm_start':False,                         #default: False
        'class_weight':'balanced_subsample'         #default: None
    }
    # replace default args with supplied arguments.
    for key, item in kwargs.tiems():
        default_args[key] = item
    # init classifier
    clf = ensemble.RandomForestClassifier(**default_args)
    return clf
```

FIG. 7

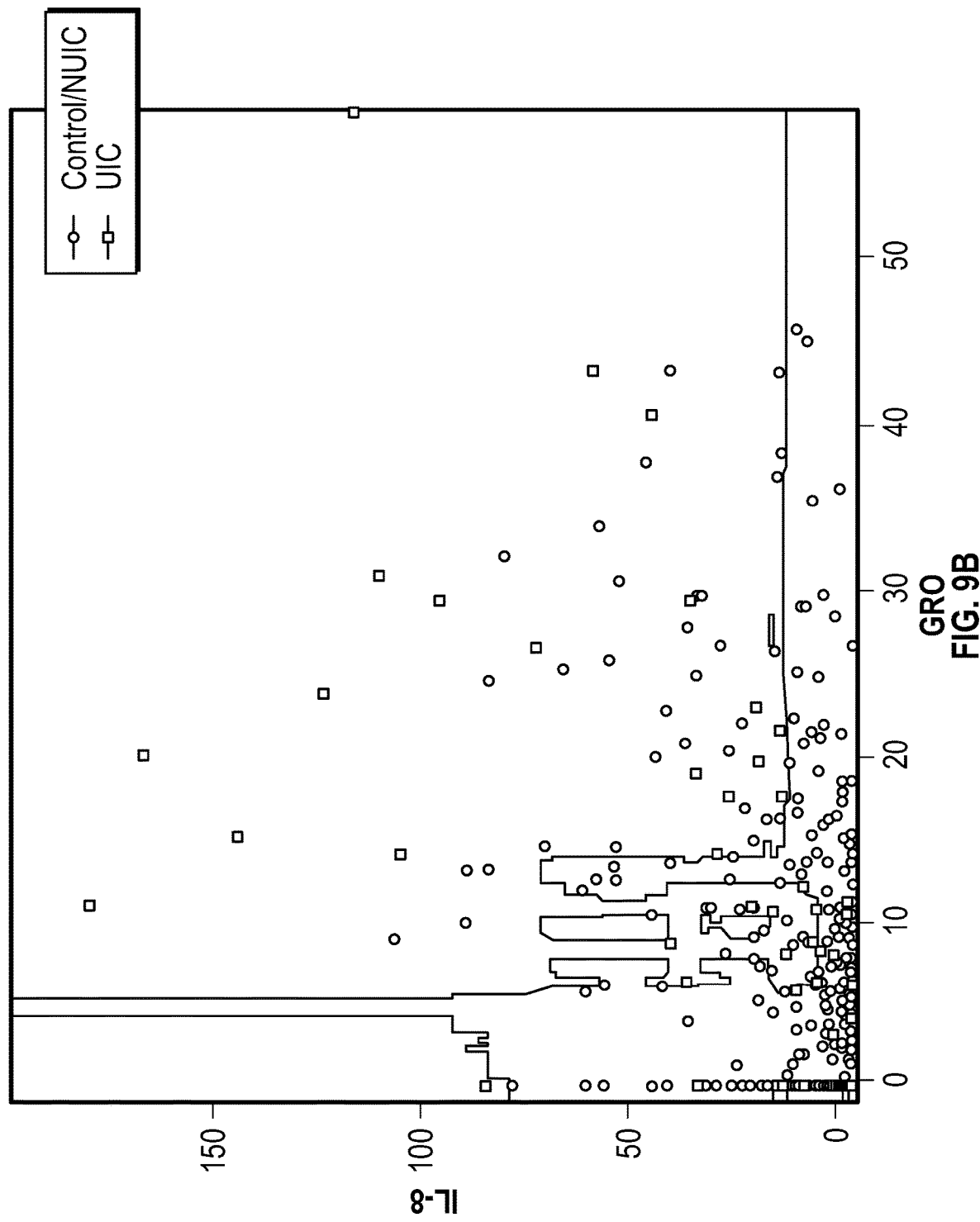

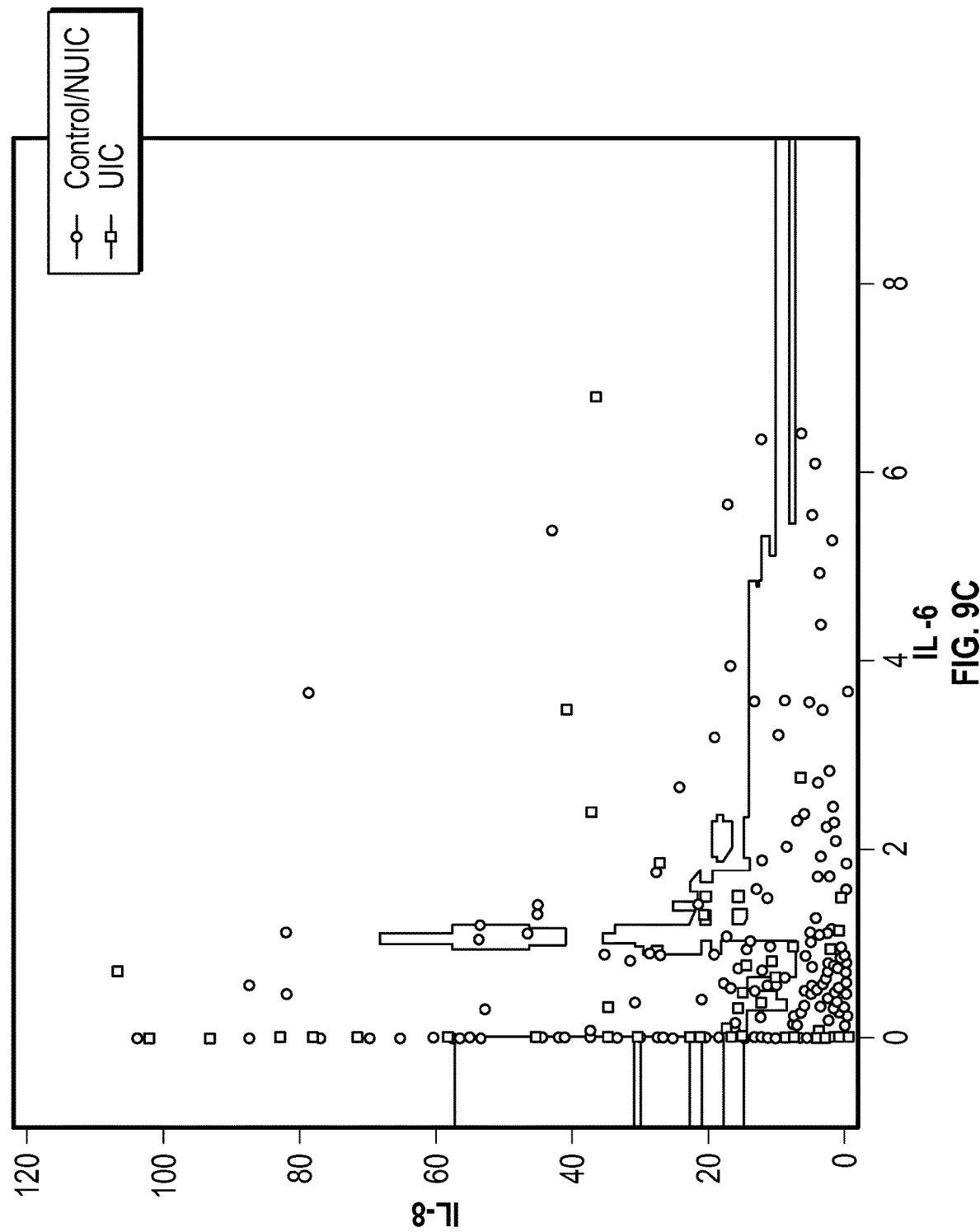

US 10,859,579 B2

METHODS FOR DETECTING, DIAGNOSING AND TREATING ULCERATIVE INTERSTITIAL CYSTITIS

CROSS-REFERENCE TO RELATED APPLICATIONS

This patent application is a 35 U.S.C. § 371 United States national phase application of, and claims priority to PCT International application No. PCT/US2017/025501 filed Mar. 31, 2017, which claims the benefit under 35 U.S.C. § 119 of U.S. Provisional Application Ser. No. 62/315,766 filed on Mar. 31, 2016, and U.S. Provisional Application Ser. No. 62/421,521 filed on Nov. 14, 2016, the disclosures of which are considered part of the disclosure of this application and are hereby incorporated by reference in their entireties.

SEQUENCE LISTING

This application incorporates by reference in its entirety the Sequence Listing entitled "088-PCT_ST25.txt" (5 kilobytes), which was created on May 9, 2017 and filed electronically on May 11, 2017.

FIELD OF THE INVENTION

The present invention is in the field of biochemistry and medicine and relates to methods for detecting, diagnosing, and/or treating ulcerative interstitial cystitis.

BACKGROUND OF THE INVENTION

It is estimated that between three and eight million women in America are affected by interstitial cystitis (IC). Although the disease is most common in women, it also affects one to four million American men and can occur in children, although few statistics on pediatric cases exist. Interstitial cystitis is characterized by recurring and often significant pelvic pain, pressure and discomfort in the bladder and pelvic region; frequent urination; and increased urinary urgency. For patients with severe interstitial cystitis, the disease can cause unrelenting pain and the need to urinate up to 60 times a day and throughout the night. These symptoms can prevent people from leaving the house or even riding in a car, making it impossible for them to work. According to the Association of Reproductive Health Professionals, over time the impact of interstitial cystitis can affect a patient's sleep, career, family life and sexual relationships, often leading to depression and a severely reduced quality of life.

The societal toll of the disease is significant as well. According to the most recent data available from the National Institute of Diabetes and Digestive and Kidney Diseases, interstitial cystitis (and the related painful bladder syndrome) was responsible for more than four million outpatient physician or clinic visits in 2000 and an outlay of $65.9 million, excluding missed work and lost productivity. There is little doubt those numbers would be significantly higher 12 years later.

IC may be associated with sensory dysfunction and/or motor dysfunction, however, because there is no reliable test for diagnosis, consistently effective treatments also are lacking, meaning sufferers may go through multiple approaches to care, usually on a trial and error basis, and often without finding any relief at all.

Currently there are two recognized subtypes of IC: non-ulcerative (NUIC) and ulcerative (UIC). 90% of IC patients have the non-ulcerative form of IC. Non-ulcerative IC presents with pinpoint hemorrhages, also known as glomerulations, in the bladder wall. However, these are not specific for IC and any inflammation of the bladder can give that appearance.

5 to 10% of IC patients have the ulcerative form of IC. UIC is a disease in which the patients have Hunner's ulcers, lesions or patches, which are red, bleeding areas or glomerulations on the bladder wall. Hunner's ulcers are not ulcers in the usual sense. They are distinctive areas of inflammation on the bladder wall. Often, patients with UIC have more severe symptoms than patients with non-ulcerative IC. UIC may involve a bladder permeability defect etiology.

Conventionally, to check for ulcerative IC, a doctor will perform a procedure called cystoscopy, passing a cystoscope through the urethra into the bladder to look inside the bladder. A cystoscopy may be uncomfortable, painful, time-consuming and expensive and may also have limited accuracy and specificity.

Thus, there is a significant need for reliable tests to aid the physician in diagnosing and treating ulcerative interstitial cystitis.

Urine samples for IC and UIC studies are often collected at academic centers where they can be spun down and frozen for shipping and storage prior to analysis. But such "cold chain" processing may not always be feasible. Thus, there is also a need for a solution where urine samples can be collected, shipped and stored at room temperature without cold chain processing.

SUMMARY OF THE INVENTION

In one aspect, disclosed is a method of diagnosing ulcerative interstitial cystitis (UIC) in a human patient where the method includes obtaining a urine sample from the human patient, wherein the urine sample includes the proteins IL-6, IL-8, and GRO; mixing the urine sample with a preservative; detecting a level of the proteins IL-6, IL-8, and GRO in the urine sample; diagnosing the patient with UIC when the levels of each of the proteins IL-6, IL-8, and GRO in the urine sample are at a different level than a statistically validated threshold for each of the respective proteins.

In some embodiments, the method further includes performing a cystoscopy or biopsy on the patient or evaluating the symptoms or history of the patient, or any combination thereof; and diagnosing the patient with UIC when (a) the levels of each of the proteins IL-6, IL-8, and GRO in the urine sample are at a different level than a statistically validated threshold for each of the respective proteins; and (b) the cystoscopy, biopsy, symptoms or history indicates UIC. In other embodiments, the method further includes administering a therapeutically effective amount of a treatment for UIC to the diagnosed patient.

In some embodiments, the patient may be diagnosed with UIC when the levels of each of the proteins IL-6, IL-8, and GRO in the urine sample are at a higher level than a statistically validated threshold for each of the respective proteins. In some embodiments, the patient is diagnosed with UIC when one or more of the levels of the proteins IL-6, IL-8, and GRO in the urine sample is at a level at least 1.5 times or 2 times greater than a statistically validated threshold for the respective protein(s). In further embodiments, the patient is diagnosed with UIC when two or more of the levels of the proteins IL-6, IL-8, and GRO in the urine sample are at a level at least 1.5 times or 2 times greater than a statistically validated threshold for each of the respective proteins. In yet a further embodiment, the patient is diagnosed with UIC when the levels of each of the proteins IL-6, IL-8, and GRO in the urine sample are at a level at least 1.5 times or 2 times greater than a statistically validated threshold for each of the respective proteins.

In some embodiments, the urine sample is not centrifuged, not refrigerated, and not frozen. In some embodiments, the urine sample is stored at an ambient temperature. For example, the urine sample is stored at a temperature between about 4° C. and about 37° C. or between about 10° C. and about 30° C.

In some embodiments, the levels of the proteins are detected by performing an ELISA. In further embodiments, the ELISA is a multiplex ELISA.

In some embodiments, the treatment for UIC includes applying a treatment in the bladder (e.g., to the bladder wall) via intravesical instillation. For examples, the treatment applied via intravesical instillation may be local analgesics, heparin, liposome, pentosan polysulfate sodium [Elmiron], antihistamines and anti-inflammatory agents or any combination thereof.

Another aspect of the invention is a method of diagnosing ulcerative interstitial cystitis (UIC) in a human patient where the method includes obtaining a urine sample from the human patient, wherein the urine sample includes the proteins IL-6, IL-8, and GRO; preserving the urine sample; detecting a level of the proteins IL-6, IL-8, and GRO in the urine sample; determining a risk score based on the levels of the proteins IL-6, IL-8 and GRO in the urine sample; and diagnosing the patient with UIC based on the risk score.

In some embodiments, the patient is diagnosed with UIC when the risk score is above a certain value, below a certain value, or within a certain range of values. In some embodiments, the risk score is determined by a risk score model that is generated by an algorithm based on a data set comprising IL-6, IL-8, and GRO levels in patient urine samples and control urine samples. The algorithm may be a machine learning algorithm. For example, the machine learning algorithm may be a classification machine learning algorithm, such as a random forest classifier algorithm. In some embodiments, the risk score model comprises a plurality of decision trees that each predict a positive or negative diagnosis for UIC based on levels of proteins IL-6, IL-8 and GRO in a subset of the data set. In some embodiments, the risk score for a urine sample is calculated by determining an average of the output values of the plurality of decision trees, wherein the output equals a first value when the decision tree predicts a negative diagnosis for UIC and the output equals a second value when the decision tree predicts a positive diagnosis for UIC. In one particular embodiment, the patient is diagnosed with UIC when the risk score is greater than 0.5.

Yet another aspect of the invention is a method of diagnosing and treating UIC in a human patient where the method includes obtaining a urine sample from the patient, wherein the urine sample includes the proteins IL-6, IL-8 and GRO; detecting a level of each of the proteins IL-6, IL-8, and GRO in the urine sample; diagnosing the patient with UIC when the levels of each of the proteins IL-6, IL-8, and GRO in the urine sample are at a different level than a statistically validated threshold for each of the respective proteins; and administering a therapeutically effective amount of a treatment for UIC to the diagnosed patient.

In some embodiments, the treatment includes applying a treatment in the bladder (e.g., to the bladder wall) via intravesical instillation. For examples, the treatment applied via intravesical instillation may be local analgesics, heparin, liposome, pentosan polysulfate sodium [Elmiron], antihistamines and anti-inflammatory agents or any combination thereof.

Another aspect of the invention is a method of diagnosing ulcerative interstitial cystitis (UIC) in a human patient where the method includes: obtaining a urine sample from the human patient, wherein the urine sample includes the proteins IL-6, IL-8, and GRO; detecting a level of each of the proteins IL-6, IL-8, and GRO in the urine sample; performing a cystoscopy or biopsy on the patient or evaluating the symptoms or history of the patient, or any combination thereof; and diagnosing the patient with UIC when (a) the levels of each of the proteins IL-6, IL-8, and GRO in the urine sample are at a different level than a statistically validated threshold for each of the respective proteins and (b) the cystoscopy, biopsy, symptoms or history indicates UIC.

In some embodiments, a cystoscopy is performed on the patient and the patient is diagnosed with UIC when (b) the cystoscopy indicates UIC.

Another aspect of the invention is a method of providing medical services for a human patient suspected of having or having UIC where the method includes: requesting a urine sample from and diagnostic information about the patient, wherein the diagnostic information is a level of each of the proteins IL-6, IL-8, and GRO in the urine sample; and administering a therapeutically effective amount of a treatment for UIC when the diagnostic information indicates that the levels of each of the proteins IL-6, IL-8, and GRO in the urine sample are at a different level than a statistically validated threshold for each of the respective proteins.

Yet another aspect of the invention is a method of providing medical services for a human patient suspected of having or having UIC where the method includes: requesting a urine sample from and diagnostic information about the patient, wherein the diagnostic information is a level of each of the proteins IL-6, IL-8, and GRO in the urine sample; performing a cystoscopy or biopsy on the patient or evaluating the symptoms or history of the patient, or any combination thereof; and diagnosing the patient with UIC when (a) the levels of each of the proteins IL-6, IL-8, and GRO in the urine sample are at a different level than a statistically validated threshold for each of the respective proteins, and (b) the cystoscopy, biopsy, symptoms or history indicates UIC.

BRIEF DESCRIPTION OF THE DRAWINGS

The foregoing summary, as well as the following detailed description of the invention, will be better understood when read in conjunction with the appended drawings. For the purpose of illustrating the invention, there are shown in the drawings, certain embodiment(s) which are presently preferred. It should be understood, however, that the invention is not limited to the precise arrangements and instrumentalities shown.

FIG. 7 is an example of computer programming language for constructing a random forest classifier model.

FIGS. 9A, 9B and 9C are decision boundary illustrations for each pair of biomarkers using the random forest classifier algorithm.

DETAILED DESCRIPTION OF THE INVENTION

Figure 1C:
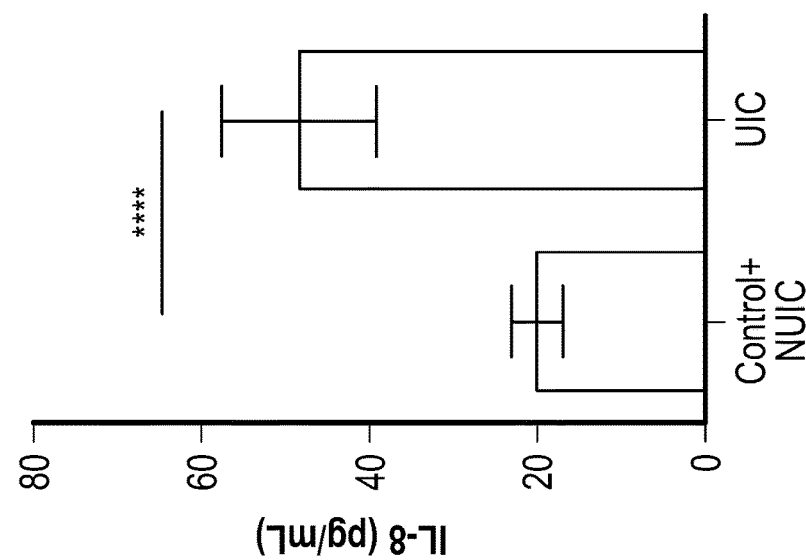
FIGS. 1A, 1B and 1C are bar charts of the mean level of proteins GRO, IL-6 and IL-8, respectively, for the control samples (control or NUIC)) and the patient samples (UIC). The units on the y-axis are pg/mL.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

All references, patents, patent publications, articles, and databases, referred to in this application are incorporated herein by reference in their entirety, as if each were specifically and individually incorporated herein by reference. Such patents, patent publications, articles, and databases are incorporated for the purpose of describing and disclosing the subject components of the invention that are described in those patents, patent publications, articles, and databases, which components might be used in connection with the presently described invention. The information provided below is not admitted to be prior art to the present invention, but is provided solely to assist the understanding of the reader.

The details of one or more embodiments of the invention are set forth in the accompanying drawings and the description below. Other features, embodiments, and advantages of the invention will be apparent from the description and drawings, and from the claims. The preferred embodiments of the present invention may be understood more readily by reference to the following detailed description of the specific embodiments and the Examples included hereafter.

For clarity of disclosure, and not by way of limitation, the detailed description of the invention is divided into the subsections that follow.

Unless defined otherwise, all technical and scientific terms used herein have the meaning commonly understood by one of ordinary skill in the art to which this invention belongs. Generally, the nomenclature used herein and the laboratory procedures in cell culture, molecular genetics, organic chemistry and protein chemistry described below are those well-known and commonly employed in the art. Although any methods, devices and materials similar or equivalent to those described herein can be used in the practice or testing of the invention, the inventive methods, devices and materials are now described.

Definitions

In this specification and the appended claims, the singular forms "a," "an" and "the" include plural reference unless the context clearly dictates otherwise.

As used in the application, "administering", when used in conjunction with a treatment means providing or performing medical services with respect to a subject in need of a treatment. For example, when used when used in conjunction with a therapeutic, administering means to deliver a therapeutic directly into or onto a target tissue or to administer a therapeutic to a subject whereby the therapeutic positively impacts the tissue to which it is targeted. "Administering" a composition may be accomplished by oral administration, injection, infusion, absorption or by any method in combination with other known techniques. "Administering" may include the act of self-administration or administration by another person such as, for example, a healthcare provider or other individual.

The terms "diagnosis" or "diagnosing" mean a determination (by one or more individuals) that the cause or nature of a problem, situation, or condition in a subject is UIC, or a confirmation of the diagnosis of the disease that includes alternative UIC diagnostics, other signs and/or symptoms (e.g., diagnosing based in whole or in part on the level(s) of the UIC-indicating proteins described herein). A "diagnosis" of UIC may include a test or an assessment of the degree of disease severity (e.g., "mild," "moderate," or "severe"), current state of disease progression (e.g., "early", "middle," or "late" stages of UIC), or include a comparative assessment to an earlier diagnosis (e.g., the UIC's symptoms are advancing, stable, or in remission). A diagnosis may include a "prognosis," that is, a future prediction of the progression of UIC, based on the observed disease state (e.g., based in whole or in part on the different level(s) of the one or more UIC-indicating proteins described herein). A diagnosis or prognosis may be based on one or more urine samples obtained from a subject, and may involve a prediction of disease response to a particular treatment or combination of treatments for UIC.

The term "subject" or "patient" as used herein generally refers to any living organism to and may include, but is not limited to, any human, primate, or non-human mammal in need of diagnosis and/or treatment for a condition, disorder or disease (e.g., ulcerative interstitial cystitis). A "subject" may or may not be exhibiting the signs, symptoms, or pathology of UIC at any stage of any embodiment.

The term "therapeutically effective amount" refers to the amount of treatment (e.g., of an active agent or pharmaceutical compound or composition) that elicits a biological and/or medicinal response in a patient, subject, tissue, or system that is being sought by a researcher, medical doctor or other clinician, or any combination thereof. A biological or medicinal response may include, for example, one or more of the following: (1) preventing a disorder, disease, or condition in an individual that may be predisposed to the disorder, disease, or condition but does not yet experience or display pathology or symptoms of the disorder, disease, or condition, (2) inhibiting a disorder, disease, or condition in an individual that is experiencing or displaying the pathology or symptoms of the disorder, disease, or condition or arresting further development of the pathology and/or symptoms of the disorder, disease, or condition, and/or (3) ameliorating a disorder, disease, or condition in an individual that is experiencing or exhibiting the pathology or symptoms of the disorder, disease, or condition or reversing the pathology and/or symptoms disorder, disease, or condition experienced or exhibited by the individual.

The term "treatment" or "treating" as used herein refers to administrating a medicine or the performance of medical procedures with respect to a subject, for either prophylaxis (prevention) or to cure or reduce the extent of or likelihood of occurrence or recurrence of an infirmity or malady or condition or event in the instance where the subject is afflicted. As related to the present invention, the term may also mean administrating medicine or the performance of medical procedures as therapy, prevention or prophylaxis of ulcerative interstitial cystitis.

The terms "ulcerative interstitial cystitis," "ulcerative IC," or "UIC" refer to a form of interstitial cystitis in which the patients have Hunner's ulcers, lesions or patches, which are red, bleeding areas or glomerulations on the bladder wall.

The term "preserved urine" as used herein refers to a urine sample that includes a preservative that inhibits protein degradation, particularly degradation of IL-6, IL-8 and GRO, in the urine sample.

The term "machine-learning" as used herein refers to a type of artificial intelligence (AI) that provides computers with the ability to learn without being explicitly programmed and can grow and change when exposed to new data. Machine-learning algorithms can be separated into two categories: classification algorithms and regression algorithms.

The term "patient sample" refers to a urine sample from a subject with a known diagnosis of UIC, such as from a data set (e.g., the IP4IC data set), or a urine sample from a subject in need of diagnosis for UIC where it is unknown whether the subject has UIC, or a urine sample from a subject suspected of having UIC.

The term "control sample" refers to a urine sample from a subject known not to have UIC, i.e., either known to have NUIC or known to have no IC.

The term "data set" refers to protein level data collected from a plurality of patient samples and control samples. The term "training data set" refers to a data set used to train a machine-learning algorithm. The term "subset" refers to a portion of a data set. A subset may be protein level data for a single patient sample or control sample or a subset may be protein level data for a small number of samples, whether control, patient or both. A subset may be a random grouping of one or more control and patient samples.

The terms "protein level" or just "level" refer to a quantifiable amount of a protein in a urine sample. The level may be an expression level from an assay for the protein such as a fluorescence level as determined by an enzyme-linked immunosorbent assay (ELISA). The level may be a concentration level of the protein in a urine sample in wt %, vol %, mol % or the like, which may be calculated from expression level data from an assay and may be based on calibration data.

UIC is conventionally diagnosed by cystoscopy with hydrodistention under anesthesia, however there are several limitations to this approach. First, glomerulations during hydrodistention can be observed in people without IC symptoms. Second, severity of IC symptoms does not always correlate with the severity of glomerulations. Lastly, hydrodistention results in the bladder being filled to a high pressure, which can cause pain or discomfort for several weeks after the procedure. Some patients may experience temporary painful urination and hematuria. There is also less common risks of puncturing the bladder wall or temporary urinary retention.

The inventors have surprisingly found that by detecting each of the proteins IL-6, IL-8 and GRO, it is possible to diagnose UIC and to differentiate between ulcerative and non-ulcerative IC. The detection and analysis of the combination of IL-6, IL-8 and GRO levels results in a synergistic effect, increasing the specificity and accuracy of diagnosis of UIC. In some embodiments, the detection levels of IL-6, IL-8 and GRO can be used to create a risk score based on algorithms generated using a training data set with levels of IL-6, IL-8 and GRO from patient and control samples.

The inventors have also surprisingly found that by using preserved urine (rather than processed urine that is kept on ice, spun down, supernatant removed and aliquoted, and frozen), the urine sample is able to maintain levels of proteins IL-6, IL-8 and GRO for detection without significant degradation of the proteins.

Urine Sample

Methods of diagnosis, detection and treatment of the invention include obtaining a urine sample. The urine sample may be a fresh urine sample that is totally unprocessed. In some embodiments, the urine sample is a preserved urine sample. The preserved urine sample comprises a preservative combined with the urine. The preservative may be any preservative known to preserve proteins in urine. That is, the preservative will inhibit significant degradation of the proteins IL-6, IL-8 and GRO in a urine sample. More specifically, in one embodiment, the preservative will inhibit between from about 20% to about 100% (e.g., from about 40% to about 80% or from about 60% to about 100%) of the protein degradation that would occur if no preservative were combined with the urine sample. The preservative may be a commercially available urine preservative. For example, the preservative may be a urine preservative available from Norgen Biotek Corp (Thorold, ON, Canada), such as Norgen catalog numbers 18118, 18120, 18111, or 18124. Urine preservatives are also discussed in US PG Pub. No. 20120021407 A1, published Jan. 26, 2012, incorporated herein by reference, which teaches tartaric acid and boric acid as known urine preservatives. The urine sample may also be preserved and stored at ambient temperatures. Ambient temperature refers to the surrounding environmental temperature of the sample. For example, the preservative may allow the storage of the urine sample at temperatures between 4 and 37 degrees Celsius (e.g., 10 to 30 degrees Celsius) or up to 55 degrees Celsius, as well as at refrigerated or frozen temperatures. The preservative may be provided in a urine sample container prior to addition of the urine, thereby providing ease of use.

The preserved urine may be an unprocessed urine sample (other than addition of the preservative). For example, the preserved urine has not undergone and does not undergo one or more, or all, of the following processing steps: storage on ice, freezing, refrigeration, centrifugation, removal of supernatant, discarding of pellet, and aliquoting of supernatant. Preserved urine samples allow for the urine to be stored (before undergoing protein level detection assays) without the need for cold chain processing. The preserved urine may allow for prolonged storage of the urine without significant degradation of proteins that would interfere with detection and diagnosis. For example, the urine may be preserved for 24 hours, 48 hours, 72 hours, 5 days, 1 week, 2 weeks, 30 days, 1 month, or 1 year without significant protein degradation.

The protein biomarkers are also compatible with traditional cold chain processing. Therefore, in another embodiment, the urine sample for use in the invention is a processed urine sample. The processed urine sample may undergo one or more, or all, of the following processing steps: storage on ice, freezing, refrigeration, centrifugation, removal of supernatant, discarding of pellet, and aliquoting of supernatant.

Detection Methods

The proteins IL-6, IL-8 and GRO have been found by the inventors to be predictive biomarkers for diagnosing UIC. The proteins IL-6, IL-8 and GRO can also be used to diagnose IC generally and to distinguish between ulcerative and non-ulcerative IC. IL-6, (interleukin 6), IL-8 (interleukin 8; also known as CXCL8), and GRO [Growth-regulated alpha protein; also known as CXCL1 (chemokine C-X-C motif ligand 1)], are cytokines that can be found in urine. The Genbank Gene ID numbers for these proteins are 3569 for IL-6, 3576 for IL-8, and 2919 for GRO. The Genbank Accession numbers for these proteins are P08505 for IL-6, P10145 for IL-8, and P09341 for GRO. The amino acid sequence for the protein IL-6 is SEQ ID NO: 1. The amino acid sequence for the protein IL-8 is SEQ ID NO: 2. The amino acid sequence for the protein GRO is SEQ ID NO: 3.

The urine sample can undergo detection for IL-6, IL-8 and GRO levels according to known techniques for protein level detection in a biological sample. The proteins may be assayed individually, in combination, or by high-throughput methods. Preferred methods are reliable, sensitive and specific for the particular protein biomarkers of the invention. The skilled artisan will recognize which detection methods are appropriate based on the sensitivity of the detection method and the abundance of the target protein.

In some embodiments, the levels of IL-6, IL-8 and GRO are detected by ELISA. In some embodiments, the levels of IL-6, IL-8 and GRO are detected by a multiplex ELISA, for example the MILLIPLEX MAP Human Cytokine/Chemokine Panel from EMD/Millipore which is based on the Luminex® xMAP® technology. In some embodiments, the protein levels are detected by high-performance liquid chromatography (HPLC), liquid chromatography-mass spectrometry (LC/MS), protein immunoprecipitation, immunoelectrophoresis, western blot, protein immunostaining, gas chromatography (GC), capillary electrophoresis (CE), desorption electrospray ionization (DESI), laser ablation ESI (LAESI), ion-mobility spectrometry, electrochemical detection, or Raman spectroscopy.

In an ELISA, an antigen is immobilized to a solid surface. It is then complexed with an antibody that is linked to an enzyme. Detection is accomplished by assessing the conjugated enzyme activity after incubation with a substrate to produce a measurable product such as but not limited to fluorescence, luminescence, chromogenic, or absorbance. The antigen can be detected either directly by a labeled primary antibody or indirectly by a labeled secondary antibody.

The principle behind Luminex® xMAP® technology is that the analyte of interest is bound by a specific capture antibody to internally color-coded microspheres (or beads) that have two fluorescent dyes. The particular combination of the concentration of dyes allows over 100 distinct color bead sets to be generated, so different analytes of interest can have different color-coded spheres, and therefore multiplexing (measuring multiple analytes of interest at the same time within the same test sample) is possible. After the analyte from the urine or test sample is bound, a biotinylated detection antibody is added. Streptavidin PE conjugate, the reported molecule, is then added to the reaction and bound to the analyte-bound microspheres. The microspheres are then passed through a series of two lasers that 1) excites the internal color-coded dyes to identify the analyte of interest, and 2) to measure and quantify the fluorescent signal on the reporter molecule.

Companion Diagnostics

In some embodiments, companion diagnostics may be performed and combined with the biomarker diagnostics of the present invention in advance of, simultaneous with, or to confirm or follow-up the biomarker-based diagnosis. Suitable companion diagnostics for UIC are known in the art. In some embodiments, the companion diagnostic for diagnosing UIC is a cystoscopy. A cystoscopy involves passing a cystoscope through the urethra into the bladder to look inside a subject's bladder. It is usually performed with hydrodistention under anesthesia. To make a diagnosis the doctor will assess the severity of glomerulations on the bladder wall (e.g., distinguish between pinpoint glomerulations and larger areas of glomerulations). In some embodiments, the companion diagnostic for diagnosing UIC is a bladder biopsy. In other embodiments, the companion diagnostic may be evaluation of the symptoms and/or history of the patient suspected of having UIC. For example, the patient may have severe symptoms, such as 24 hour urinary frequency of greater than 10 or an IC symptom score in the moderate to severe category. Other symptoms include pelvic pain, pressure in the bladder, discomfort in the bladder or in the pelvic region, frequent urination, nocturia, decreased force of urination, urgency, urinary incontinence, pain during sexual intercourse. A symptom score may be produced based on one or more of symptoms of IC and/or UIC. In some embodiments, the patient is diagnosed with UIC (a) if the level of proteins IL-6, IL-8 and GRO in a urine sample from the patient is at a different level than a statistically valid threshold and (b) if the companion diagnostic also indicates UIC.

One aspect of the invention is a method of providing medical services for a human patient suspected of having or having UIC, the method comprising: requesting a urine sample from and diagnostic information about the patient, wherein the diagnostic information is a level of each of the proteins IL-6, IL-8, and GRO in the urine sample; performing a cystoscopy or biopsy on the patient or evaluating the symptoms or history of the patient, or any combination thereof; and diagnosing the patient with UIC when (a) the levels of each of the proteins IL-6, IL-8, and GRO in the urine sample are at a different level than a statistically validated threshold for each of the respective proteins, and (b) the cystoscopy, biopsy, symptoms, or history indicates UIC. For example, the method may include ordering a diagnostic test for UIC based on the levels of IL-6, IL-8 and GRO from a laboratory that performs such testing.

Statistical Methods

In some embodiments, the statistically validated threshold is used to diagnose a subject with UIC. In other embodiments, the statistically validated threshold may also be used to diagnose a subject with IC or to distinguish between NUIC and UIC. The statistically validated threshold is based on a data set with protein level data for control samples and patient samples. The control population may be defined as subjects that do not have IC, subjects that have non-ulcerative IC, or both groups together. Various control populations are described herein. Either control group, (a) no IC or (b) NUIC, or the combined control group, (c) no IC and NUIC, can all be used interchangeably with the methods of the invention, including calculating the statistically validated threshold. The statistically validated thresholds are related to the values used to characterize the level of the specific proteins in the urine sample obtained from the subject or patient. Thus, if the level of the protein is an absolute value, then the control value is also based upon an absolute value.

The statistically validated thresholds can take a variety of forms. For example, a statistically validated threshold can be a single cut-off value, such as a median or mean. Or, a statistically validated threshold can be divided equally (or unequally) into groups, such as low, medium, and high groups, the low group being individuals least likely to have UIC and the high group being individuals most likely to have UIC.

Statistically validated thresholds, e.g., mean levels, median levels, or "cut-off" levels, may be established by assaying a large sample of individuals in the select population (patients and controls) and using a statistical model such as the predictive value method for selecting a positivity criterion or receiver operator characteristic curve that defines optimum specificity (highest true negative rate) and sensitivity (highest true positive rate). A "cutoff value" may be separately determined for the level of each specific protein assayed. Statistically validated thresholds also may be determined according to the methods described in the Examples hereinbelow.

The levels of the assayed proteins in the patient urine sample may be compared to single control values or to ranges of control values. In one embodiment, the specific proteins (IL-6, IL-8 and GRO) in a urine sample from a patient (e.g., a patient having or suspected of having UIC) are present at a different level (e.g., at an elevated level) compared to the same specific proteins in control samples from subjects that do not have UIC when the level of the specific proteins in the patient urine sample is at least 1.1 times greater than the statistically validated threshold (e.g., mean concentration) for the control samples. For example, the proteins are present at a different level when the levels of proteins IL-6, IL-8 and GRO in a sample are each at least 1.1×, at least 1.2×, at least 1.25×, at least 1.3×, at least 1.4×, at least 1.5×, at least 1.6×, at least 1.7×, at least 1.75×, at least 1.8×, at least 1.9×, at least 2×, at least 2.1×, at least 2.2×, at least 2.25×, at least 2.3×, at least 2.4×, at least 2.5×, at least 3×, at least 3.5×, at least 4×, at least 4.5×, at least 5×, at least 6×, at least 7×, at least 8×, at least 9×, or at least 10×, greater than the statistically validated threshold (e.g., mean concentration) for the respective protein in the control samples.

In some embodiments, the methods comprise diagnosing the patient with UIC when the levels of the proteins IL-6, IL-8, and GRO in the urine sample are at a higher level than a statistically validated threshold for the proteins IL-6, IL-8, and GRO; and one or more of the levels of the proteins IL-6, IL-8, and GRO in the urine sample is at a level at least 1.1 times (e.g., at least 1.1×, at least 1.2×, at least 1.25×, at least 1.3×, at least 1.4×, at least 1.5×, at least 1.6×, at least 1.7×, at least 1.75×, at least 1.8×, at least 1.9×, at least 2×, at least 2.1×, at least 2.2×, at least 2.25×, at least 2.3×, at least 2.4×, at least 2.5×, at least 3×, at least 3.5×, at least 4×, at least 4.5×, at least 5×, at least 6×, at least 7×, at least 8×, at least 9×, or at least 10×) greater than a statistically validated threshold for the respective protein.

In some embodiments, the methods comprise diagnosing the patient with UIC when the levels of the proteins IL-6, IL-8, and GRO in the urine sample are at a higher level than a statistically validated threshold for the proteins IL-6, IL-8, and GRO; and two or more of the levels of the proteins IL-6, IL-8, and GRO in the urine sample are at a level at least 1.1 times (e.g., at least 1.1×, at least 1.2×, at least 1.25×, at least 1.3×, at least 1.4×, at least 1.5×, at least 1.6×, at least 1.7×, at least 1.75×, at least 1.8×, at least 1.9×, at least 2×, at least 2.1×, at least 2.2×, at least 2.25×, at least 2.3×, at least 2.4×, at least 2.5×, at least 3×, at least 3.5×, at least 4×, at least 4.5×, at least 5×, at least 6×, at least 7×, at least 8×, at least 9×, or at least 10×) greater than a statistically validated threshold for each of the respective proteins.

If the level of a specific protein or proteins in the patient urine sample are present at different levels than their respective statistically validated thresholds, then the patient is more likely to have UIC than are individuals with levels comparable to the statistically validated threshold. The extent of the difference between the subject's levels and statistically validated thresholds is also useful for characterizing the extent of the risk and thereby, determining which individuals would most greatly benefit from certain therapies, e.g., aggressive therapies. In those cases, where the statistically validated threshold ranges are divided into a plurality of groups, such as statistically validated threshold ranges for individuals at high risk of UIC, average risk of UIC, and low risk of UIC, the comparison involves determining into which group the subject's level of the relevant risk predictor falls.

A "different level" or "elevated level" of a protein refers to the amount of expression or concentration of a protein in a urine sample from a patient compared to statistically validated thresholds, e.g., the amount of the protein in urine sample(s) from individual(s) that do not have UIC, have UIC (or a particular severity or stage of UIC), have NUIC, have no IC, or have other reference diseases. For example, a protein has an "elevated level" in the urine from a subject when the protein is present at a higher concentration in the subject's urine sample than in urine from a subject who does not have UIC. For the proteins IL-6, IL-8 and GRO, elevated levels in a urine sample indicate the presence of or a risk for UIC.

In some embodiments, the protein levels are used to diagnose IC, NUIC or to distinguish NUIC from UIC. For example, as shown in FIGS. 2A-D and Tables 5 and 6, below, the protein expression levels of IL-6, IL-8 and GRO for subjects with no IC, NUIC and UIC may each be differentiated from each other. Therefore, a statistically validated threshold may be used based on the levels of IL-6, IL-8 and GRO in a data set to diagnose IC generally, to diagnose NUIC, or to distinguish between NUIC and UIC.

Therefore, in some embodiments, the methods further comprise diagnosing the patient with IC when the levels of the proteins IL-6, IL-8, and GRO in the urine sample are at a different level (e.g., a higher level) than a statistically validated threshold for the proteins IL-6, IL-8, and GRO. In some embodiments, the methods further comprise diagnosing the patient with NUIC when the levels of the proteins IL-6, IL-8, and GRO in the urine sample are at a different level (e.g., a higher level) than a statistically validated threshold for the proteins IL-6, IL-8, and GRO.

Risk Scores

In some embodiments, a risk score is used to diagnose a subject with UIC. For example, one aspect of the invention comprises obtaining a urine sample from the human patient, wherein the urine sample includes the proteins IL-6, IL-8, and GRO; detecting a level of the proteins IL-6, IL-8, and GRO in the urine sample; determining a risk score based on the levels of the proteins IL-6, IL-8 and GRO in the urine sample; and diagnosing the patient with UIC based on the risk score. The risk score may be a value from 0 to 1, 0-10, 0-100, 1-10, 1-100, −1 to 1, etc. The risk score is calculated based on a data set comprising known control samples (no IC and/or NUIC) and patient samples (UIC). The data set includes information for each patient or control sample about whether or not the sample is from a patient with a positive UIC diagnosis, and may also differentiate whether the sample is from a subject with a NUIC diagnosis or no IC. The data set also includes information about the levels of IL-6, IL-8 and GRO in each urine sample from the patient or control.

The risk score model (used to calculate a risk score) may be generated using an algorithm. In some embodiments, the algorithm is a machine-learning algorithm. The machine learning algorithm is able to analyze data from a large data set, e.g., a training data set, and analyze trends in the data to create a model for calculating a risk score. Many machine-learning algorithms may be appropriate for creating a risk score model using a data set. Machine learning algorithms are of two types: classification and regression algorithms. Classification algorithms were generally found to give better specificity for the data set but regression algorithms can also be used successfully. There are many categories of and particular examples of classification algorithms that can be used with the data set. For example, ensemble, Bayesian, decision tree, and neural network algorithms can be used. As discussed in the examples below, the random forest classifier algorithm is a preferred algorithm for using with the data set.

To create the risk score model, the machine learning algorithm is trained on a data set. The diagnosis data (yes UIC or no UIC) and protein level data (concentration or expression level) from each patient and control sample can be used to create a plurality of decision trees. The plurality of decision trees can then be used as a model for calculating a risk score. For example, each decision tree can lead to an outcome of 0 or 1, depending on whether the individual decision tree would find a negative (0) or positive (1) diagnosis based on the protein levels in a new urine sample. The risk score can be calculated as an average of these outcomes from all of the decision trees generated by the machine-learning algorithm.

Figure 8:
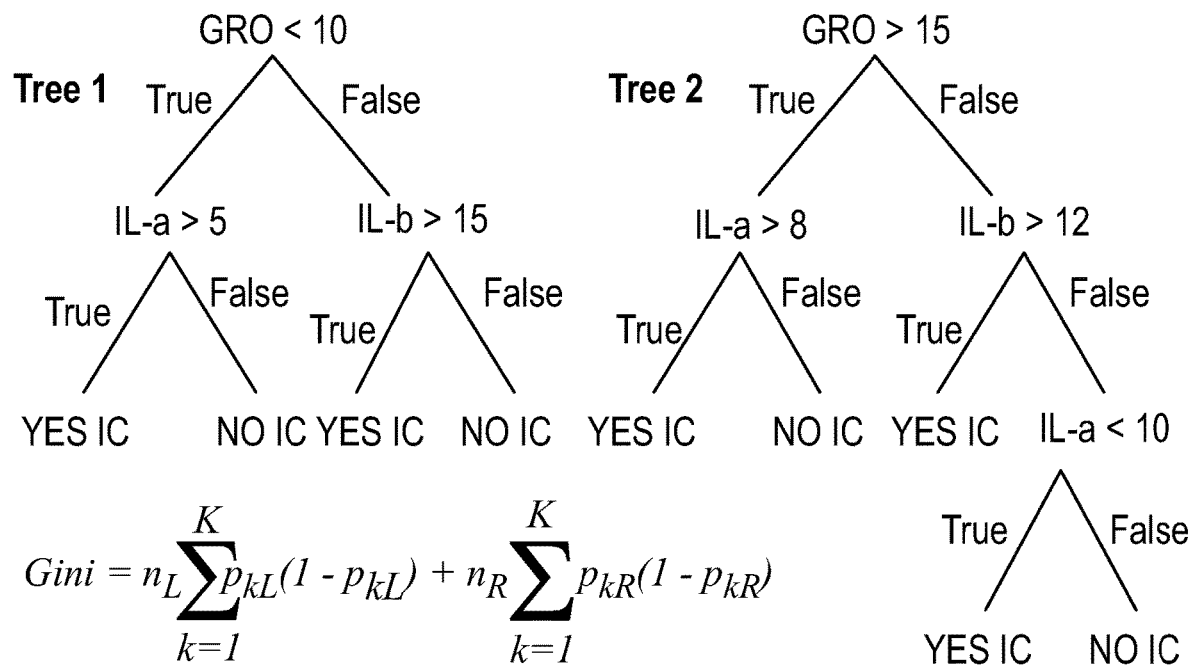
FIG. 8 is an example of two decision trees generated from random subsets of the data set, where "IL-a" is IL-6 and "IL-b" is IL-8.

The decision trees are generated from random subsets of the data set. The random subset may be defined as the protein levels from one UIC patient sample, one NUIC control sample and one no IC control sample. A decision tree can be generated from this subset. Two example decision trees are shown in FIG. 8. For example, in FIG. 8, if a patient presents with GRO=12, IL-a=7 and IL-b=9, then the total YES IC Votes=2 and the total NO IC Votes=0. The ICUS calculated from these votes=0.99; therefore, it is likely that the patient has ulcerative IC. The ICUS uses hundreds of these random decision trees for high prediction accuracy.

Methods of Diagnosis and Treatment

In some embodiments, if a patient is diagnosed with UIC according to the above-described diagnostic methods, then the patient is treated for UIC. The patient may be treated with any known treatments for UIC. In some embodiments, the treatment includes applying a treatment in the bladder (e.g., coating the bladder wall) via intravesical instillation. For example, the treatment applied via intravesical instillation may be local analgesics, heparin, liposome, pentosan polysulfate sodium [Elmiron], antihistamines and anti-inflammatory agents or any combination thereof.

For example, the treatment may comprise administration of oral pharmacologic agents such as pentosan polysulfate sodium [Elmiron], antihistamines, tricyclic antidepressants, analgesics, anti-inflammatory agents; intravesical therapy (medications instilled directly into the bladder via a catheter); surgical therapies; electrical simulation; or complementary or holistic therapies such as acupuncture, hypnosis, or pelvic floor massage.

One aspect of the invention is a method of providing medical services for a human patient suspected of having or having UIC, the method comprising: requesting a urine sample from and diagnostic information about the patient, wherein the diagnostic information is a level of each of the proteins IL-6, IL-8, and GRO in the urine sample; and administering a therapeutically effective amount of a treatment for UIC when the diagnostic information indicates that the levels of each of the proteins IL-6, IL-8, and GRO in the urine sample are at a different level than a statistically validated threshold for each of the respective proteins. For example, the method may include ordering a diagnostic test for UIC based on the levels of IL-6, IL-8 and GRO from a laboratory that performs such testing.

The term "therapeutically effective amount" is defined above and includes an amount of treatment that elicits a biological and/or medicinal response in a patient that is being sought by a treating physician.

Kits

Another embodiment of the present invention is a kit for diagnosing UIC. Kits that allow for the targeted measure of the proteins IL-6, IL-8, and GRO would reduce both overall cost and turn-around time for a diagnosis of UIC.

In one embodiment, a biomarker panel is used to diagnose UIC by detecting IL-6, IL-8, and GRO levels in the sample. The inventive kit for diagnosing UIC may include (a) an ELISA-based assay for detecting the protein levels; (b) a container for the urine sample; and (c) instructions for the method of detection. The kit may further comprise a preservative for the urine. In some embodiments, the preservative is contained within the container in the kit.

In one embodiment, the present diagnostic methods and kits are useful for determining if and when medical treatments and therapeutic agents that are targeted at treating UIC should or should not be prescribed for an individual patient. Such medical treatments and therapeutic agents are discussed above and/or are known in the art, and will be ordered by or prescribed by a physician (or other healthcare provider) based on results of the inventive method and standard medical practices.

EXAMPLES

Example 1: Sample Population for Data Set

A) IP4IC Data Set 448 urine samples from 46 US states consisting of 153 IC patients (147 female, 6 male), of which 54 were UIC patients (50 female, 4 male), 159 female controls and 136 male controls were collected through a crowd sourcing effort in collaboration with the Interstitial Cystitis Association (ICA) with Beaumont IRB approval. Controls were age-matched. Study eligibility included United States mailing address, and ability and willingness to provide a urine sample and return it by mail. Exclusion criteria was urinary tract infection or any surgical prostate therapies (biopsies, microwave, needle ablation, balloon dilation, laser procedure, cryosurgery) within the last three months, or pregnancy. IC (ulcerative and non-ulcerative) participants had a reported physician diagnosed case for over 6 months. To evaluate in a more universal target population than just one geographical area and to collect a large cohort, we conducted a study on a crowdsourced control, NUIC, and UIC samples termed IP4IC. These samples were collected by individuals in their homes and not in a clinical setting.

B) P3 Data Set 51 midstream urine samples from UIC, NUIC and control participants were collected at Beaumont Hospital in Royal Oak, Mich. All participants provided written consent. Asymptomatic controls had no history of IC, recurrent urinary tract infection, bladder or prostate cancer, or kidney disease. Exclusion criteria were unable to complete questionnaires or unable to provide urine specimen.

Example 2: Detection Methods

MILLIPLEX MAP Human Cytokine/Chemokine Panel from EMD/Millipore which is a multiplex ELISA assay based on the Luminex® xMAP® technology was used to detect the protein levels in the urine sample collected according to Example X. A Human cytokine standard was generated using reagents provided by the manufacturer and following the manufacturer's instructions a serial dilution was generated (5 concentrations with range of 3.2-2,000 pg/mL; the 0 pg/ml standard (background) was assay buffer). Median Fluorescent Intensity (MFI) data from 50 beads per set was measured. A 5-parameter logistic or spline curve-fitting method was used to calculate cytokine/chemokine concentrations in samples. Protein levels for patients confirmed with UIC were compared to levels for controls and patients with NUIC. The protein levels were measured using Luminex technology to quantify of a panel urinary cytokines. Concentrations of the cytokines were determined by comparison to a standard curve.

The detection was performed for the urine samples collected in Example 1. Protein levels of IL-6, IL-8 and GRO were determined for the urines samples. The levels were used to generate a data set containing the protein level information and diagnosis information (UIC, NUIC or no IC) for each sample.

Example 3: Selection of Algorithm for UIC Risk Score

Data obtained from Example 1 from IC patients and controls was used to build a machine-learning algorithm model. The model provides a probability of UIC, i.e. a risk score, when the algorithm is supplied with the levels of the three proteins, IL-6, IL-8 and GRO in a urine sample. The three protein levels in combination provide a much better prediction model than any of these individual protein levels alone. The ICUS code was written in the Python programming language utilizing the scikit-learn library for machine learning.

The Random Forest Classifier (RFC) was identified as the best algorithm for generating the ICUS. A Random Forest is a meta estimator that fits a number of classifying decision trees on various sub-sets of the data set and uses averaging to improve the predictive accuracy and to control overfitting. In essence, the RFC will create many different decision trees from random sub-samples of the training data (from IP4IC data set, Example 1), and the terminal (leaf) nodes of the trees will be associated with a probability for which class (ulcerative IC or not) the data fed into the tree fits in to. The RFC is the most stable algorithm tested on the IP4IC.

The RFC model is built from a labeled training dataset (from the IP4IC data set). The "model" is a Python object (piece of code in the computer program) that contains all of the decision trees, and it is used as a predictor for new data. When provided the levels of three different proteins found in urine, it will run these data through the decision trees and, from the tree results, calculates a probability score. The model can be used as it was trained with the IP4IC dataset, or it can be regenerated when data is obtained from new patients outside of the dataset. Adding new training data to the model will generally result in better prediction accuracy.

Random Forest algorithms are broadly categorized with other ensemble algorithms. It is also considered to be a decision tree algorithm, as the Random Forest is an ensemble of random decision trees. There are classification and regression versions of many machine learning algorithms. For this problem type (i.e. the ICUS score prediction), classification algorithms are the most suitable as we have distinct classes (ulcerative IC vs no IC/non-ulcerative IC).

The machine learning algorithm that is used for the prediction can be considered as modular; a number of different algorithms could be substituted for the random forest classifier. Many of the ensemble, decision tree, Bayesian, and neural network algorithms could be substituted. Not all of these were tested with the IP4IC dataset, but the random forest had the best performance of the algorithms that were tested.

Example 4: Training the Machine-Learning Algorithm

The IP4IC dataset contains crowdsourced urology data from control, NUIC and UIC patients. It contains entries for condition (control or IC) and ulcer (yes or no). The Python program generates a new column, training set label, based on the values of these two columns. A control patient gets a label value of 0, an IC patient without hunner's ulcers gets a label value of 0, and an IC patient with hunner's ulcers gets a label value of 1. This dataset also contains the levels of three proteins (GRO, IL-6, and IL-8) that are part of the training data used to build the decision trees. The biomarker training data are given as concentrations and are not normalized, since this generally degrades the performance of a random forest algorithm. Table 1 shows an example of what the training set looks like. Only a subset of the complete dataset is shown in Table 1. The Training Set Label column does not originally exist in the IP4IC dataset, but is generated from the Condition and Ulcer columns. The fourth through seventh columns shows the training set used to build the RFC model. In machine learning terminology, the Training Set Label column would be called "labels", "targets", or "classes", and the protein data columns would be called "samples" or "training data samples".

TABLE 1

Format of IP4IC data.

| Patient Number | Condition | Ulcer | Training Set Label | Protein 1 level (GRO) | Protein 2 level (IL-6) | Protein 3 level (IL-8) | ... |
|---|---|---|---|---|---|---|---|
| 1 | Control | No | 0 | # | # | # | ... |
| 2 | IC | No | 0 | # | # | # | ... |
| 3 | IC | Yes | 1 | # | # | # | ... |
| ... | ... | ... | ... | ... | ... | ... | ... |

Table 2 shows summary statistics for the biomarkers of interest including the means of the protein levels in the IP4IC data set.

TABLE 2

Summary Data of IP4IC Dataset.

| | Mean ± SEM | | |
|---|---|---|---|
| Protein | No IC/Non-ulcerative IC | Ulcerative IC | Change |
| GRO | 11.7 ± 1.6 | 19 ± 3.8 | +63% |
| IL-6 | 1.7 ± 0.6 | 3.2 ± 1.5 | +85% |
| IL-8 | 21.2 ± 3.4 | 47.8 ± 9.4 | +125% |

The following are steps that are followed to build the trained RFC. This process may differ slightly for other machine learning algorithms, but the essential steps are to read in the training data, initialize the model (whether it be random forest or something else), and then train the model with the data. The training data become 'baked in' to whatever model is chosen (in this case, via the decision trees).

1. The IP4IC dataset is read into program. The only columns that are used from this dataset are the 'Condition', 'Ulcer', 'GRO', 'IL-6', and 'IL-8'. (Note that additional proteins that are correlated with the presence of ulcerative IC could be used. This method is not limited to using just three proteins)

2. The training set labels are calculated from the 'Condition' and 'Ulcer' columns, as described above.

3. The RFC Python object is then initialized with optimized parameter arguments (FIG. 7).

FIG. 7 shows the parameters used to build the Random Forest Classifier Model. These parameters were chosen from an optimization of the RFC model. Optimization was performed by varying the parameters and then calculating the out-of-bag (OOB) error estimate. Performance and accuracy of machine learning methods is typically assessed with cross-validation; however, the Random Forest method has an internal validation measure called the out-of-bag (OOB) error estimate. This score is continually calculated when building the trained classifier and updated by testing each decision tree on the data that was not included in the random subset used to build the three. The parameters that provided the highest OOB were chosen and are shown here. Any changes to the training set will likely change the optimal parameters. It is important to note here that the random_state argument is provided a value instead of the default 'None'. The implication of setting this number is that if the RFC is trained with the same exact data set at some point in the future, the 'random' decision trees that are generated when the RFC is trained will be identical. They are still pseudo-random in nature, but setting this key lets allows for regenerating the same pseudo-randomness given identical training data. The code library used for the RFC constructor (ensemble.RandomForestClassifier) is provided by the scikit-learn package for python. The clf variable in the above code contains the (untrained) RFC model.

After the RFC is constructed, there is an RFC python object ready to be trained. At this point, there are no decision trees since training data has not yet been fit to the model.

4. The RFC python object is trained by fitting the following data to the RFC object:

a. Sample Data: The protein data (from the 'GRO', 'IL-6', and 'IL-8' columns) as a vector of 3-vectors.

b. Target Data: The training set labels (0's and 1's) as a flat vector.

To construct each decision tree (90 total in this case), a random sub-sample of the training data is taken. The data is in three dimensions, with one dimension for each of the three biomarkers. The data is split along one of the axes. The axis/point where the data is split is the point that maximizes information gain (i.e. entropy) from the split. That split can occur e.g. on axis 'IL-6' at 0.3. This translates to a node in the decision tree which says that if IL-6 of an input sample is less than or equal to 0.3, go left in the decision tree, if not, then go right. After the first split, a split may occur on the 'GRO' axis at 22 after going 'left' at the first node, and this will create a new node. The splitting of the data and node generation continues until the gini impurity, which is a measure of misclassification, is minimized (usually to 0).

At each node, there are associated class probabilities; that is, the probability that the patient does not have ulcerative IC and the probability that the patient does have ulcerative IC. The probability that the patient does have ulcerative IC (pUIC) is what is used to calculate the risk score. When a new patient's data (not used to train the model) is run through the decision trees, there will be a final, terminal node that is reached in each tree, and each node will have its own pUIC associated with it. The average of all 90 pUIC values is the final probability that the patient has ulcerative IC. This probability is what we have named the "ICUS."

Random Forests are parameterized, and a script was written to test combinations of reasonable parameters. A variety of parameters and ranges of values that were tested (Table 3). The Cartesian product (i.e. all combinations) of each value in all ranges of input variables were tested to train the classifier. Optimal results were determined (Table 4).

TABLE 3

Parameter ranges for optimization of classifier.

| Parameter | Description | Range |
|---|---|---|
| n_estimators | Number of decision trees in forest. | [10, 100], step = 1 |
| criterion | Criteria by which to make a decision to split a tree node. | ['gini', 'entropy'] |
| max_features | Number of features to consider when splitting data. | [1, 2, 3, $\sqrt{n\_features}$] |
| max_depth | Maximum depth of tree. | [None] (no limit imposed on tree depth) |
| min_samples_split | Minimum number of samples required to split an internal node. | [2] |
| min_samples_leaf | Minimum number of samples required to be at a leaf node. | [1, 30], step = 1 |
| min_weight_fraction_leaf | Minimum weighted fraction of the sum total of weights required to be at a leaf node. | [0] |
| max_leaf_nodes | Limits total number of leaf nodes. | [None] (no limit placed on total number of nodes) |
| bootstrap | Whether bootstrap samples are used when building trees. | [True] |
| oob_score | Whether OOB score is calculated when building trees. | [True] |
| n_jobs | Number of parallel jobs to run. | [−1] (uses all available processors/cores) |
| random_state | Seed value for random number generator. By default no random seed is set. | [42] (arbitrarily chosen so trees can be rebuilt if needed) |
| class_weight | Weights associated with each class (ulcerative IC = 1 or no IC/nonulcerative IC = 0) of data. | ['balanced_subsample'] & splits of 0 = X %, 1 = Y % for (X in 10 -> 90, step = 10 and Y in 90 -> 10, step = 10) |

There were 16,000 total combinations tested in this optimization. The set of parameters that maximized the accuracy of prediction of the validation set and also had the highest out-of-bag error estimate were selected as the optimal parameter set.

TABLE 4

Optimal parameters that resulted in highest OOB score for training set.

| Parameter | Value |
|---|---|
| n_estimators | 22 |
| criterion | 'gini' |
| max_features | $\sqrt{3}$ |
| max_depth | None |
| min_samples_split | 2 |
| min_samples_leaf | 3 |
| min_weight_fraction_leaf | 0 |
| max_leaf_nodes | None |
| bootstrap | True |
| oob_score | True |
| n_jobs | −1 |
| random_state | 42 |
| class_weight | 'balanced_subsample' |

Figure 9A:
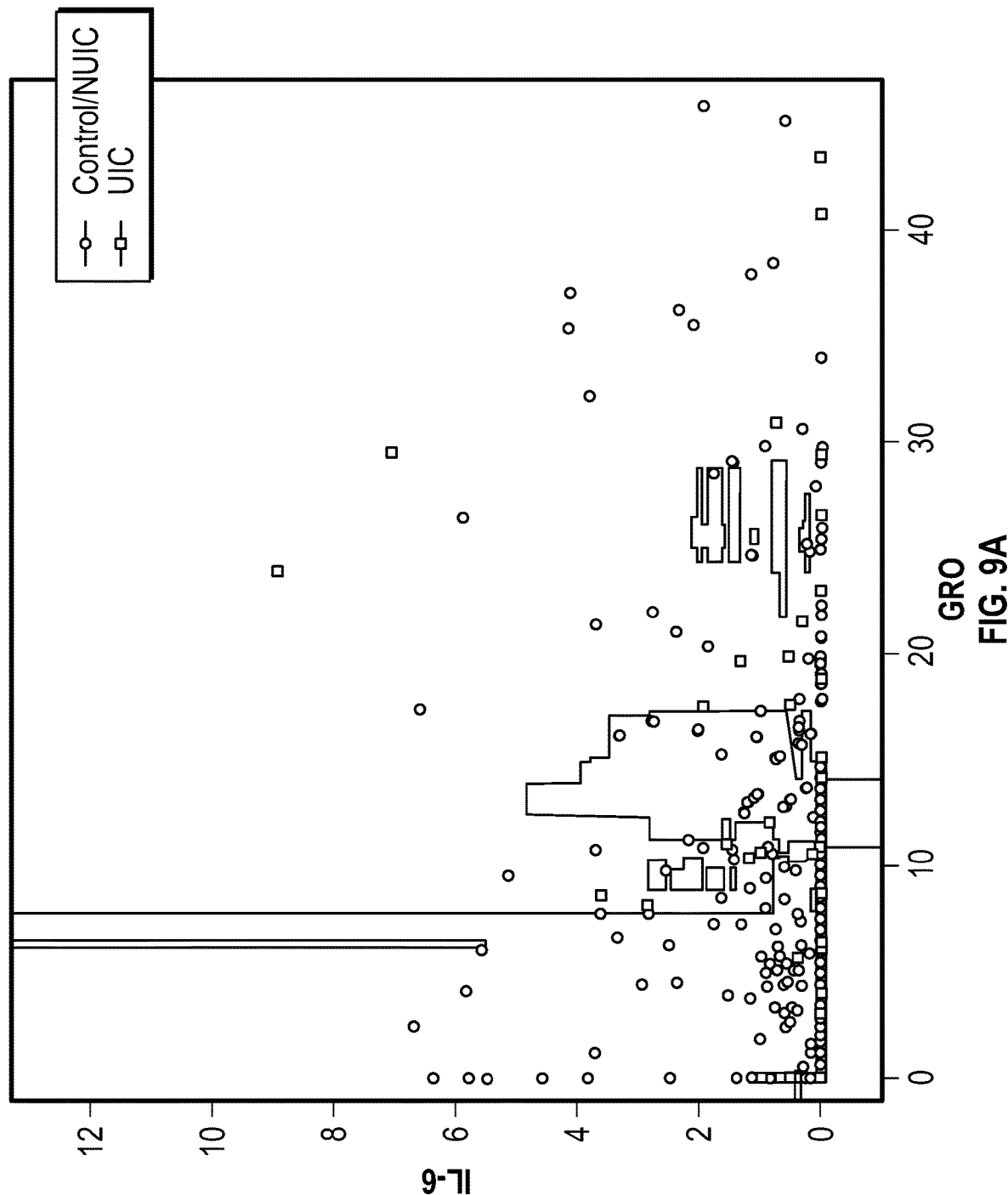

FIGS. 9A, 9B and 9C show the decision boundaries for each pair of biomarkers. The surfaces indicate UIC or non-UIC (i.e., control or NUIC). These surfaces are visual depictions translated from the decision trees. If a point exists in the UIC surface (white surface) of all three plots, then there would be a high probability that a patient with those levels of biomarkers would have UIC.

Using the random forest classifier method the relative importance of each cytokine used to make a classification was determined. IL-8 contributed most significantly toward the predictions (48%), followed by GRO (33%) and IL-6 (19%), which made smaller, but still significant contributions.

Example 5: Protein Specificity

Figure 1B:
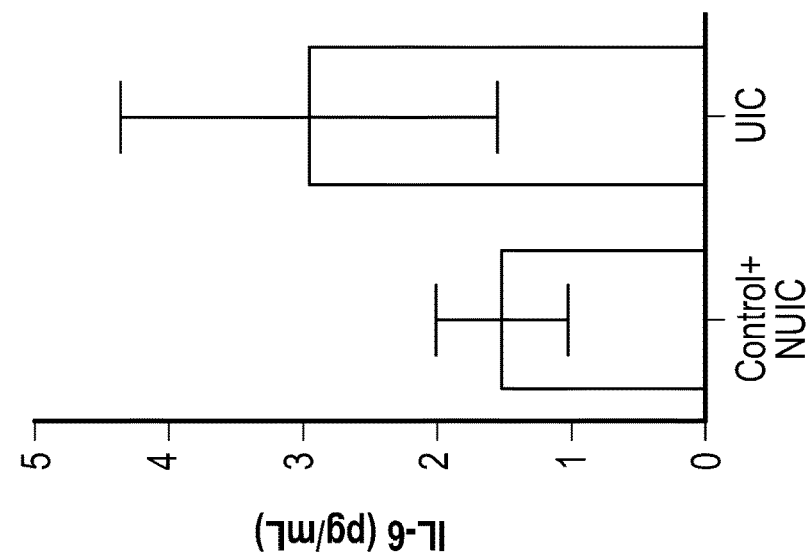
Figure 1A:
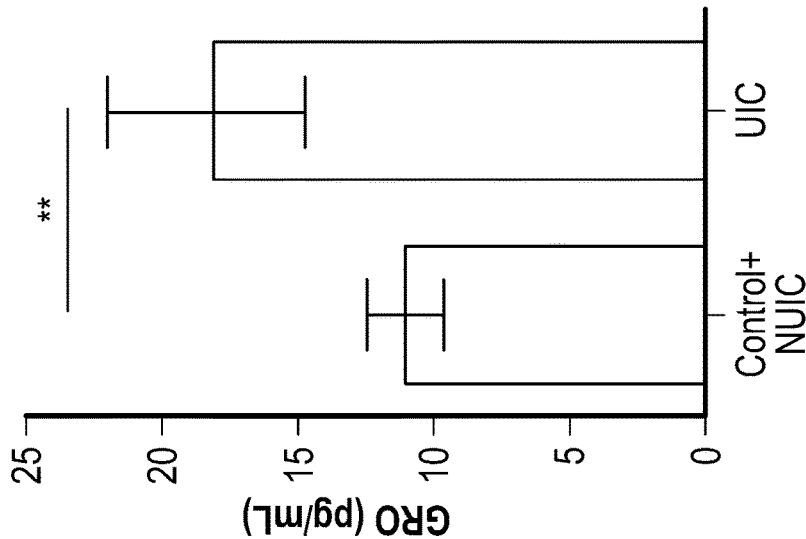
Figures 2A, 2B, 2C:
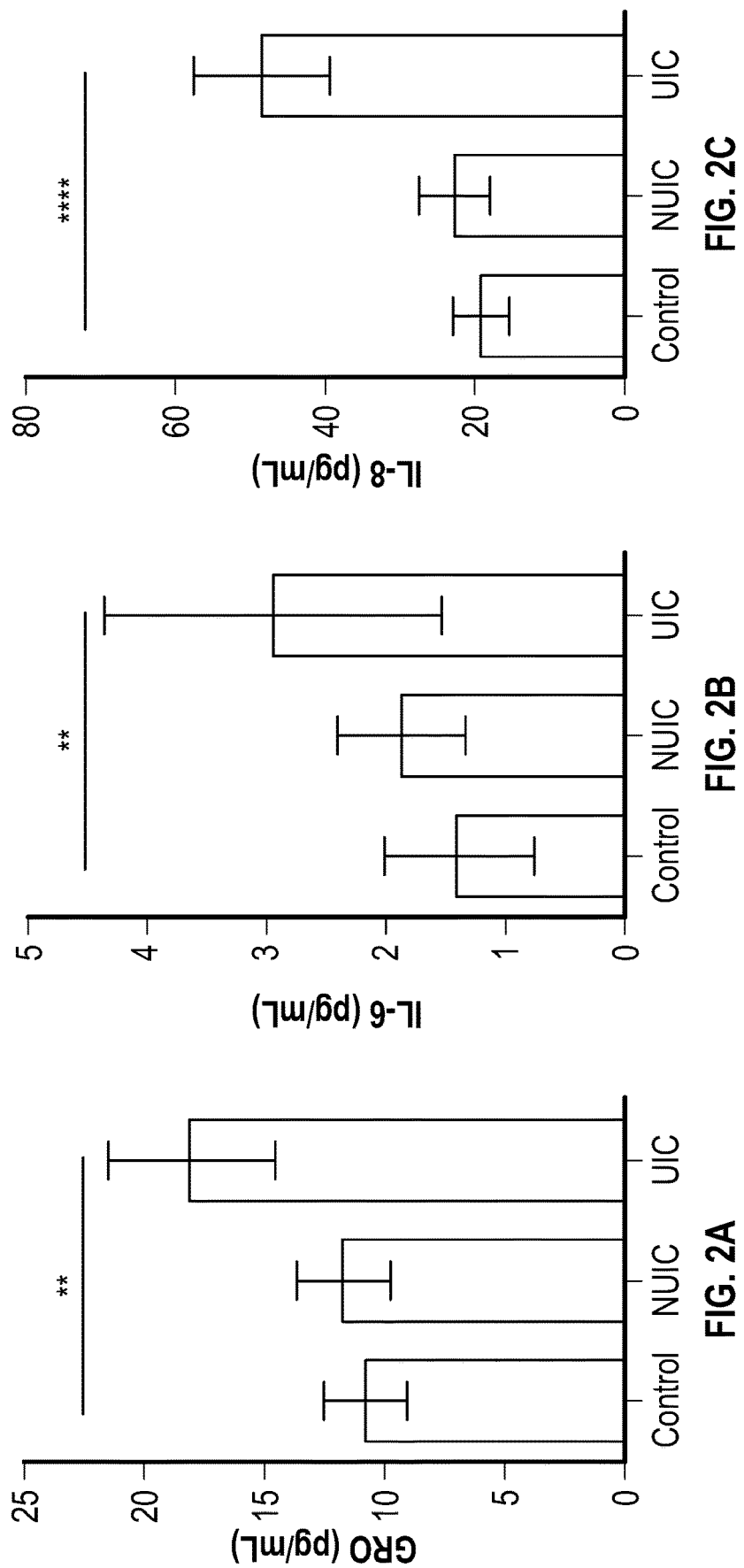
FIGS. 2A, 2B and 2C are bar charts similar to those in FIGS. 1A-C but with separate bars for the first control group with no IC (left), the second control group with non-ulcerative IC (NUIC) (center) and the patient group with ulcerative IC (UIC) (right). The units on the y-axis are pg/mL.

The specificity of the proteins for UIC was analyzed using detection of the proteins in urine samples as described herein. The levels of IL-6, IL-8, GRO were detected in a set of patient and control urine samples. The mean protein levels for patients having UIC were plotted against those of patients and control not having UIC in FIGS. 1A-C. The mean protein levels for patients having UIC were plotted against those of patients having NUIC and no IC in FIGS. 2A-C. The results show the specificity of these protein levels for UIC. The GRO, IL-6 and IL-8 levels were significantly higher in patients with UIC than in the control and NUIC groups. The results are also shown in Table 5.

TABLE 5

Urinary cytokine levels by group

|  | GRO (pg/mL) | IL-6 (pg/mL) | IL-8 (pg/mL) |
|---|---|---|---|
| Controls + NUIC | 11.07 ± 1.41 | 1.52 ± 2.97 | 20.17 ± 3.03 |
| UIC | 18.06 ± 3.50 | 2.96 ± 1.41 | 48.61 ± 9.04 |
| p-value | 0.0026 | 0.1479 | <0.0001 |
| Control | 10.83 ± 1.78 | 1.40 ± 0.63 | 15.72 ± 2.85 |
| NUIC | 11.74 ± 1.98 | 1.97 ± 0.54 | 24.84 ± 4.79 |
| UIC | 18.06 ± 3.50 | 2.96 ± 1.41 | 47.77 ± 6.27 |
| p-value | 0.0065 | 0.0074 | <0.0001 |

The data from Table 5 was used to calculate fold change values for cytokines GRO, IL-6, and IL-8 for controls and/or non-ulcerative IC compared to ulcerative IC as shown in Table 6.

TABLE 6

Fold change values

| | Fold Change | | |
|---|---|---|---|
| | GRO | IL-6 | IL-8 |
| Ulcerative IC? | | | |
| No (control and IC - no ulcer) | 1.0 | 1.0 | 1.0 |
| Yes (IC - ulcer) | 1.63 | 1.95 | 2.41 |
| Group | | | |
| Control | 1.0 | 1.0 | 1.0 |
| IC - No Ulcer | 1.08 | 1.40 | 1.58 |
| IC - Ulcer | 1.67 | 2.11 | 3.04 |

A different urinary cytokine, MCP-1, was also measured in control, NUIC and UIC patients. The mean MCP-1 levels were not significantly higher in patients with UIC than in the control and NUIC groups, demonstrating the relative specificity of IL-6, IL-8 and GRO compared to other proteins found in urine. The results are shown in Table 7.

TABLE 7

MCP-1 levels by group

| | MCP-1 (pg/mL) |
|---|---|
| Controls + NUIC | 310.676 ± 15.687 |
| UIC | 331.063 ± 40.756 |
| Control | 319.991 ± 18.202 |
| NUIC | 284.063 ± 30.767 |
| UIC | 330.946 ± 40.283 |

Example 5: Evaluation of ICUS Risk Score

Once the machine-learning algorithm program has been trained on the data set, it can be used to calculate a probability that the patient has ulcerative IC, i.e. the ICUS. Protein levels from a urine sample can be evaluated via the model to calculate the ICUS. The values for these proteins are fed into the model via the predict_proba( ) method provided by the RFC python object. The values are run through the decision trees, which result in a yes or no diagnosis for UIC assigned the value 0 (no) or 1 (yes). The algorithm takes the average of these decision trees yielding a 0 or 1 to arrive at a risk score between 0 and 1 indicating the probability that the patient has ulcerative IC.

The training set was run through the algorithm to get probabilities for the values that were used to generate the model. These were used to define risk score ranges used to conclude whether a patient has ulcerative IC. The risk scores from the training set are plotted in FIG. 3.

Figure 3:
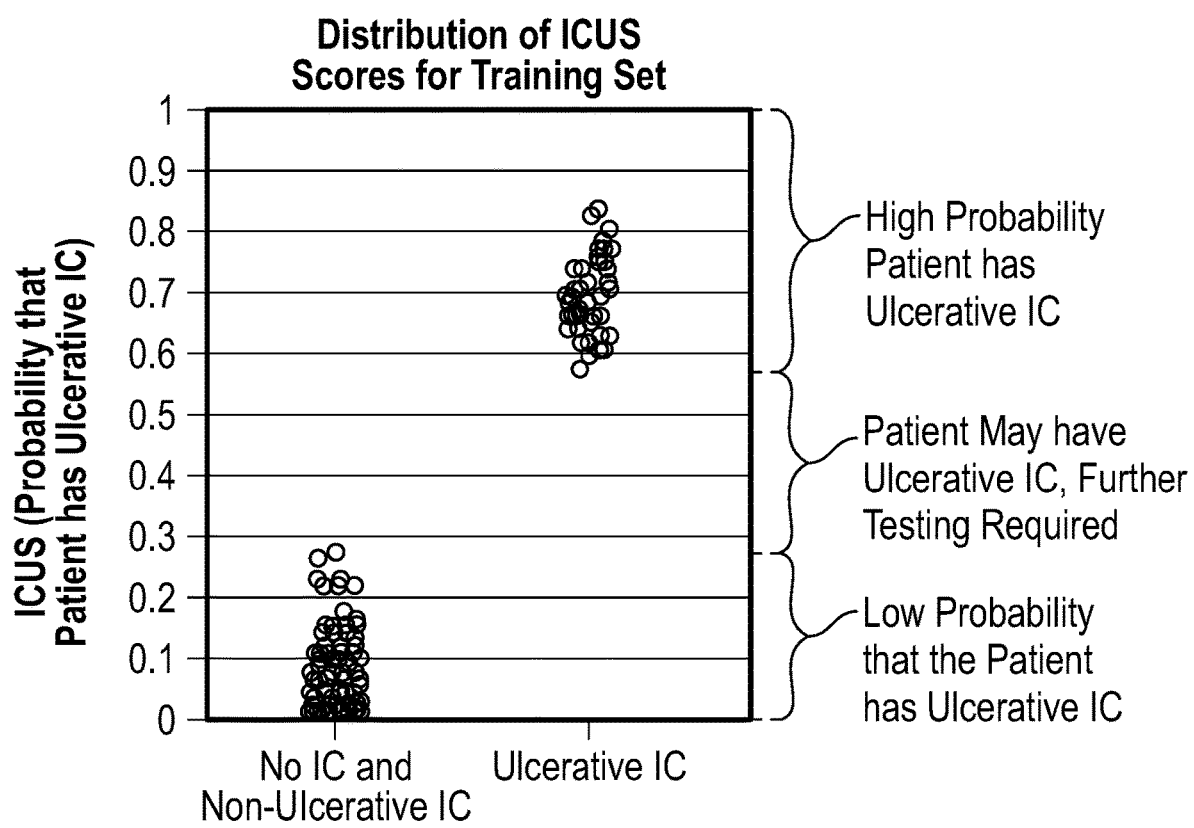
FIG. 3 is a plot of risk scores (ICUS) for control samples (No IC and NUIC, on the left) versus patient samples (UIC, on the right). The brackets on the right edge of the plot show the distinct regions for the control samples, the patient samples and the "distance measure" region between those regions.

FIG. 3 shows the ICUS distribution of the training data. Each of the training data points were fed to the trained RFC, and the ICUS was calculated for each. The points are separated visually on the x-axis to show how the scores look for each group. All of the ICUS scores for the no IC/non-ulcerative IC patients are below 0.28, and all of the scores for the ulcerative IC patients are above 0.58.

From these results, ranges may be defined for how to categorize the scores. For example, for all ICUS<0.28, there is high probability that the patient does not have ulcerative IC. For all ICUS>0.58, there is high probability that the patient does have ulcerative IC and any scores that fall between these bounds would require further diagnostic testing to aid interpretation of the score (via e.g. cystoscopy). Other ranges may also be extrapolated from this data set. For example, a score <0.4 could be interpreted as no UIC, 0.4-0.55 as undetermined, and >0.55 as UIC.

Alternatively, using the classical definition of a binary random forest classifier the values could be split at about 0.5. For example, if the ICUS is >0.5, then there is an 81.5% chance that the patient has ulcerative IC. If the ICUS is <0.5, there is an 81.5% chance that the patient does not have ulcerative IC. The 81.5% comes from the out-of-bag error estimate.

Example 6: Validation of ICUS on P3 Data Set

The ICUS score algorithm was validated in an independently conducted study, termed the P3 study. This was used to assess if the accuracy of the classifier was reasonably close to the OOB score that was calculated. To test the classifier, the P3 training set was read into a program blinded, and the protein values were fed into the trained classifier. The protein data is run through the decision trees, and the average of the classes of all the decision trees is used to classify the patient. For example, if there are 15 of 20 total trees that classify the patient as having UIC, there is a 0.75 probability that the patient has UIC. Whenever this average probability is >=0.5, the patient is predicted to have (i.e. is assigned the class of) 1 (UIC), otherwise it is assigned 0 (control or NUIC).

Figure 10:
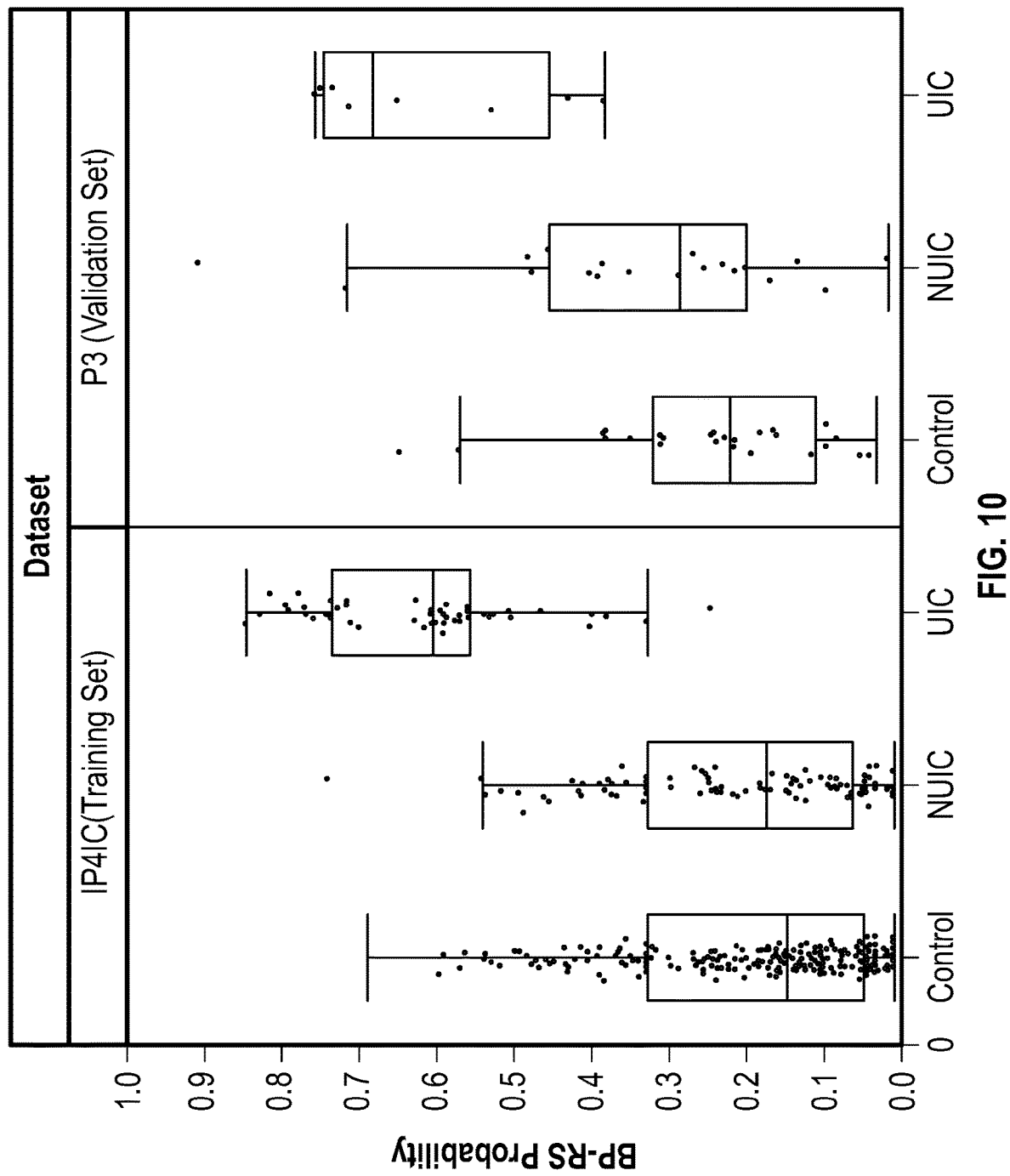
FIG. 10 is a box plot of the risk scores (ICUS) for the training (IP4IC) and validation (P3) data sets.

Patients were excluded from both the training and validation sets if protein data was incomplete (e.g. analyte detection was out-of-range). During collection of the IP4IC and P3 datasets, some values for protein levels were marked as being outside detection limits; patients missing data for even one of the protein analytes were excluded. Not all controls completed the questionnaires were assumed to be missing at random. As such, analysis of control questionnaires was based on the available data. The results of the validation are shown in FIG. 10. The bars on the boxes describe the minimum and maximum points and the horizontal lines of the box show the 25%, 50% (median), and 75% quartiles. Points outside the box are outliers. In the P3 validation set, 6 out of 8 (75%) of the UIC patients were correctly predicted to have UIC. 41 out of 45 (91.1%) of the control or NUIC patients were correctly predicted to not have UIC. Overall, 88.7% of the entire validation set was correctly predicted. This result can be expected to converge to the OOB error estimate (81.5%) if more validation test samples were present, and it may be possible to increase the OOB error estimate with an expanded training set.

Example 7: Synergy of the Combination of IL-6, IL-8 and GRO

There is a synergistic effect of using all three proteins IL-6, IL-8 and GRO as biomarkers versus any of the proteins alone or in pairs. Using all three data points allows for the best separation of the ICUS between a positive and negative diagnosis for UIC.

The random forest classifier model was trained with each of the following protein groups: GRO only, IL-6 only, IL-8 only, GRO/IL-6, GRO/IL-8, IL-6/IL-8, and GRO/IL-6/IL-8.

The parameters for building the decision trees were identical for each of the groups. For each protein group classification model, all of the relevant training data was run through the model and an ICUS was obtained for each patient.

Figure 4:
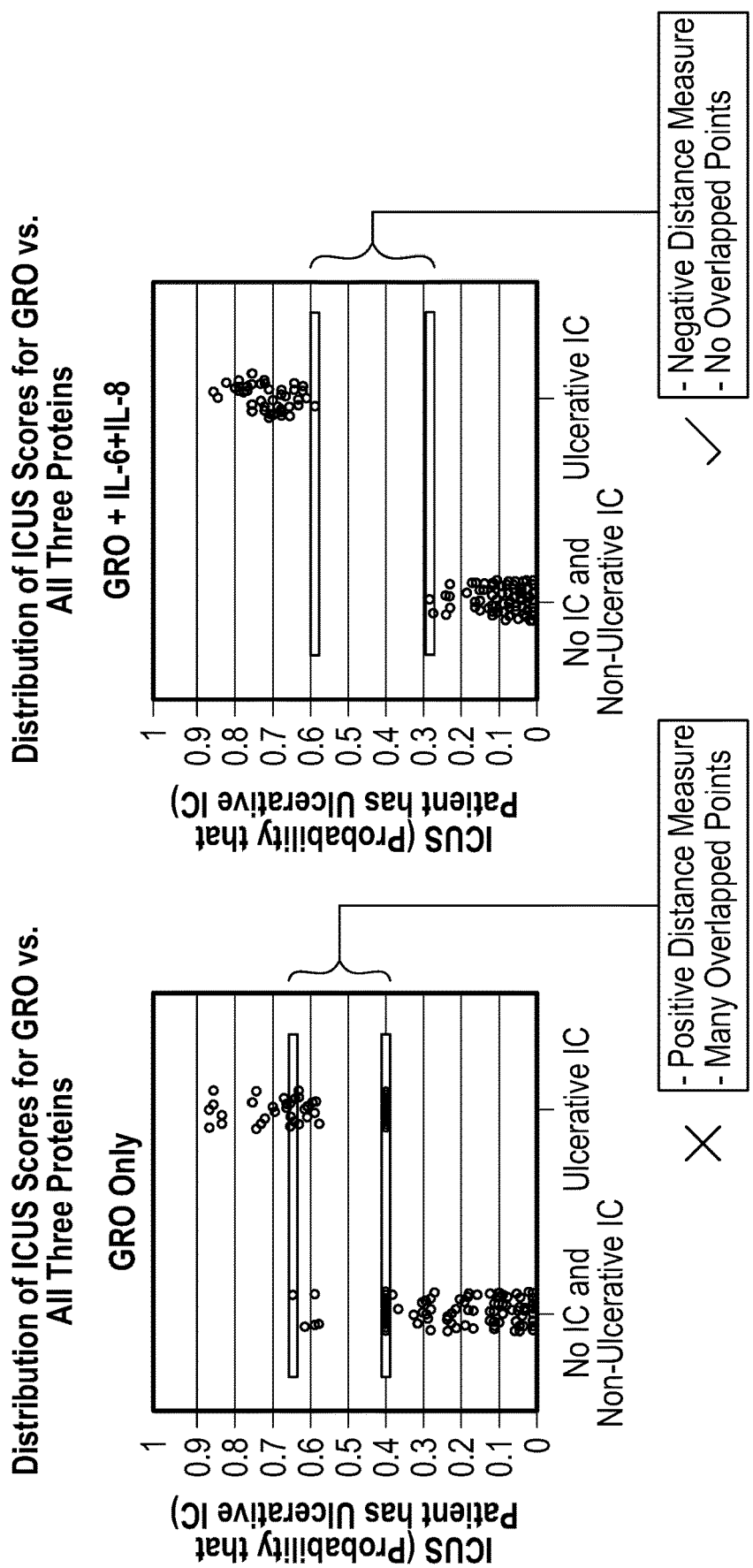
FIG. 4 is a comparative plot, similar to FIG. 3, showing the distance measure and overlapped points for risk scores generated based on GRO data only, compared to a distance measure and overlapped points for risk scores generated based on GRO, IL-6 and IL-8 data.

FIG. 4 shows the distance metric, defined as the distance between the maximum score of the non-ulcerative IC group and minimum score of the ulcerative IC group. When the distance is positive, that means there is overlap in the probabilities between the two classes. This leads to decreased prediction performance, so it is best to minimize the distance metric, with negative distance being desired.

To determine the amount of overlap for each protein group, the maximum of the non-ulcerative IC (NIC) group and the minimum of the ulcerative IC (UIC) group ICUS scores were found. Two different metrics were calculated from these maximum and minimum values. The first metric is the distance between the maximum and minimum. The second metric is the number of overlapping points that lie between this max and min.

Figure 5:
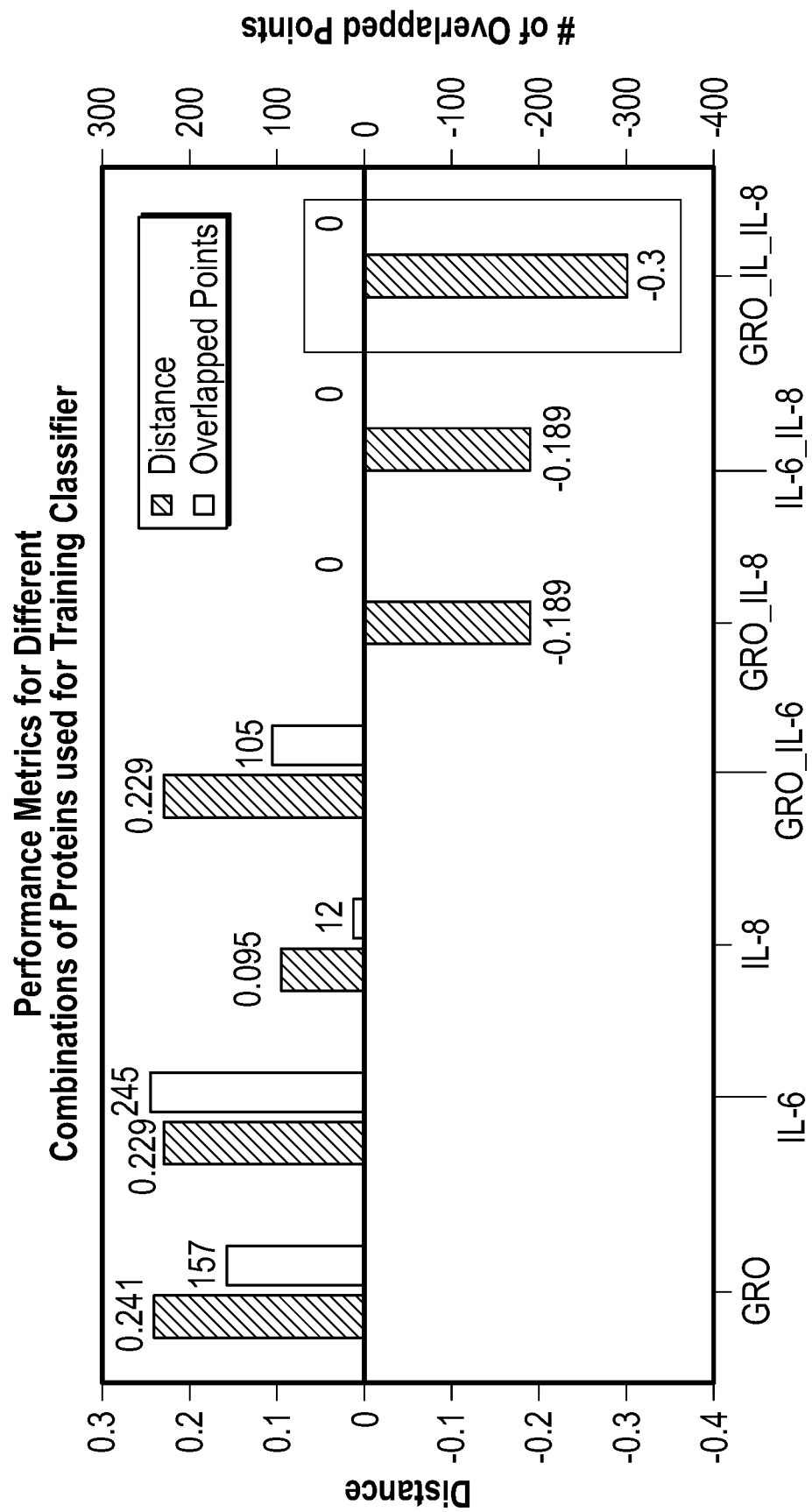
FIG. 5 is a bar chart of the distance measure and number of overlapped points, calculated as shown in FIGS. 3 and 4, as determined for risk scores generated using data from GRO only, IL-6 only, IL-8 only, GRO and IL-6, GRO and IL-8, IL-6 and IL-8, and GRO, IL-6 and IL-8.
Figure 6:
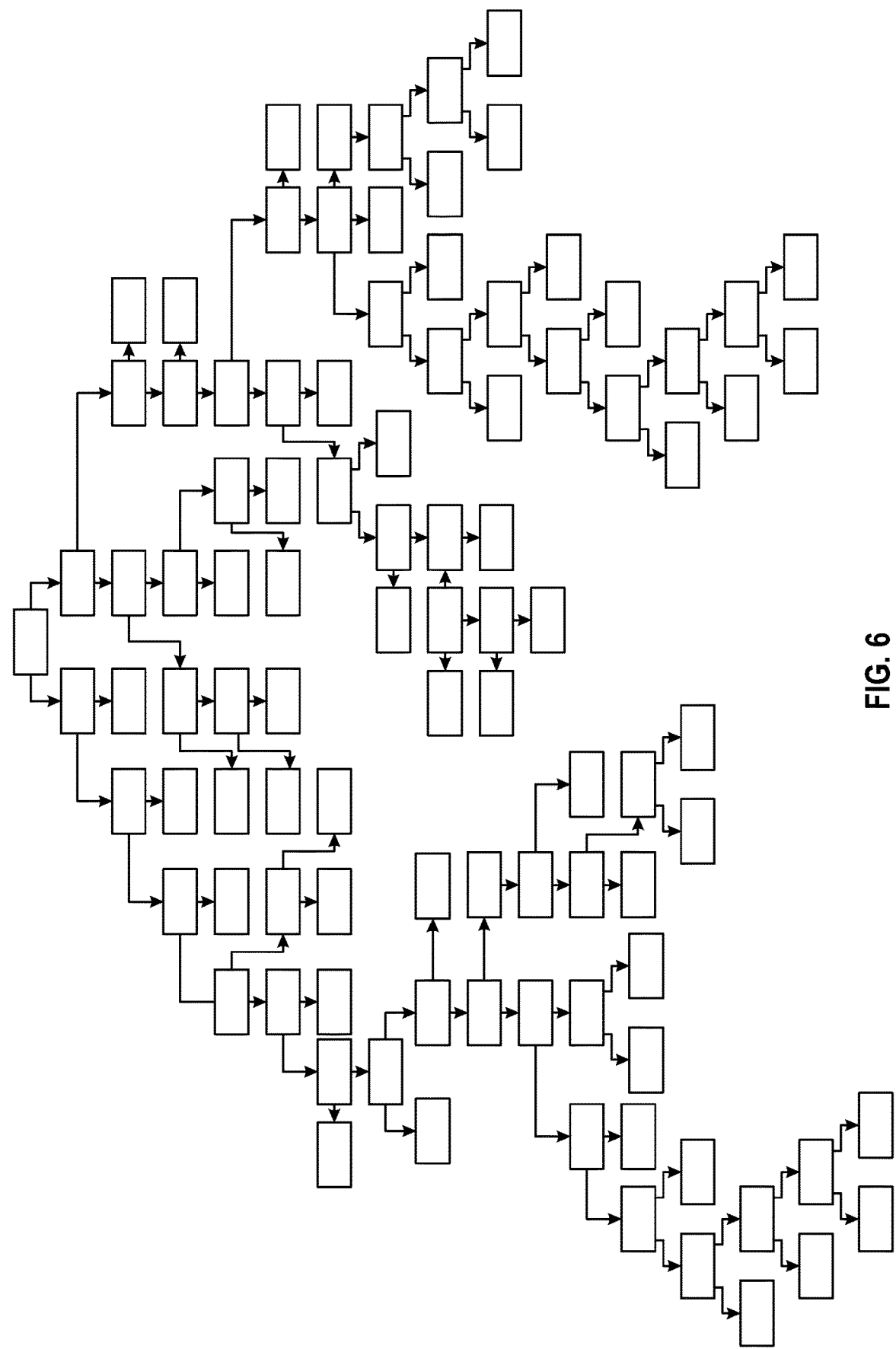
FIG. 6 is an example of a decision tree generated using the training data set.

FIG. 5 shows the results of these calculations for each protein group. The best-case scenario is that there is no overlap between groups (i.e. negative distance metric) and zero overlapping points. Therefore, it is desirable to use the protein grouping that has the lowest distance scores and lowest number of overlapping points. This was found to be the case when all three proteins were used to train the model. This is highlighted in FIG. 5.

As shown in FIG. 5, using all three proteins to train and test the model minimized the distance score (−0.3) and the number of overlapped points (0). It also had the best out-of-bag error estimate (81.5%). All others were <81.5%.

What is claimed is:

1. A method of diagnosing and treating ulcerative interstitial cystitis (UIC) in a human patient, the method comprising:
    obtaining a urine sample from the patient, wherein the urine sample includes the proteins Interleukin 6 (IL-6), Interleukin 8 (IL-8) and Growth-regulated alpha protein (GRO);
    detecting a level of each of the proteins IL-6, IL-8, and GRO in the urine sample;
    diagnosing the patient with UIC when the levels of each of the proteins IL-6, IL-8, and GRO in the urine sample are at a higher level than a statistically validated threshold for each of the respective proteins; and
    administering a therapeutically effective amount of a treatment for UIC to the diagnosed patient.

2. The method of claim 1, wherein the treatment is selected from a local analgesic, heparin, a liposome, pentosan polysulfate sodium, an antihistamine, an anti-inflammatory agent, and any combination thereof.

3. The method of claim 1, wherein the treatment is applied in the bladder via intravesical instillation.

4. The method of claim 1, further comprising performing a cystoscopy or biopsy on the patient or evaluating the symptoms or history of the patient, or any combination thereof; and diagnosing the patient with UIC when (a) the levels of each of the proteins IL-6, IL-8, and GRO in the urine sample are at a higher level than a statistically validated threshold for each of the respective proteins; and (b) the cystoscopy, biopsy, symptoms or history indicates UIC.

5. The method of claim 1, wherein the patient is diagnosed with UIC when one or more of the levels of the proteins IL-6, IL-8, and GRO in the urine sample is at a level at least 1.5 times greater than a statistically validated threshold for the respective protein(s).

6. The method of claim 5, wherein the patient is diagnosed with UIC when one or more of the levels of the proteins IL-6, IL-8, and GRO in the urine sample is at a level at least 2 times greater than a statistically validated threshold for the respective protein(s).

7. The method of claim 5, wherein the patient is diagnosed with UIC when two or more of the levels of the proteins IL-6, IL-8, and GRO in the urine sample are at a level at least 1.5 times greater than a statistically validated threshold for each of the respective proteins.

8. The method of claim 7, wherein the patient is diagnosed with UIC when two or more of the levels of the proteins IL-6, IL-8, and GRO in the urine sample are at a level at least 2 times greater than a statistically validated threshold for each of the respective proteins.

9. The method of claim 7, wherein the patient is diagnosed with UIC when the levels of each of the proteins IL-6, IL-8, and GRO in the urine sample are at a level at least 1.5 times greater than a statistically validated threshold for each of the respective proteins.

10. The method of claim 9, wherein the patient is diagnosed with UIC when the levels of each of the proteins IL-6, IL-8, and GRO in the urine sample are at a level at least 2 times greater than a statistically validated threshold for each of the respective proteins.

11. The method claim 1, wherein the urine sample is not frozen before the detection step.

12. The method of claim 11, wherein the urine sample is stored at an ambient temperature.

13. The method of claim 12, wherein the urine sample is stored at a temperature between about 4° C. and about 37° C.

14. The method of claim 13, wherein the urine sample is stored at a temperature between about 10° C. and about 30° C.

15. The method of claim 1, wherein the levels of the proteins are detected by performing an ELISA.

16. The method of claim 15, wherein the ELISA is a multiplex ELISA.

17. A method of diagnosing and treating ulcerative interstitial cystitis (UIC) in a human patient, the method comprising:
    obtaining a urine sample from the human patient, wherein the urine sample includes the proteins Interleukin 6 (IL-6), Interleukin 8 (IL-8) and Growth-regulated alpha protein (GRO);
    preserving the urine sample;
    detecting a level of the proteins IL-6, IL-8, and GRO in the urine sample from the human patient;
    determining a risk score based on the levels of the proteins IL-6, IL-8 and GRO in the urine sample from the human patient, wherein the risk score is determined by a risk score model that is generated by one or more processors comprising a machine learning algorithm based on a data set comprising IL-6, IL-8, and GRO levels in patient urine samples and control urine samples, and wherein the risk score indicates a probability that the patient is in need of treatment for UIC;
    diagnosing the patient with UIC when the risk score is greater than or equal to 0.5; and
    administering a therapeutically effective amount of a treatment for UIC when the patient is diagnosed with UIC.

18. The method of claim 17, wherein the treatment is selected from a local analgesic, heparin, a liposome, pentosan polysulfate sodium, an antihistamine, an anti-inflammatory agent, and any combination thereof.

19. The method of claim 17, wherein the machine learning algorithm is a classification machine learning algorithm or a random forest classifier algorithm.

20. The method of claim 17, wherein the risk score model comprises a plurality of decision trees that each predict a positive or negative diagnosis for UIC based on levels of proteins IL-6, IL-8 and GRO in a subset of the data set.

21. The method of claim 20, wherein the risk score for a urine sample is calculated by determining an average of the output values of the plurality of decision trees, wherein the output equals a first value when the decision tree predicts a negative diagnosis for UIC and the output equals a second value when the decision tree predicts a positive diagnosis for UIC.

22. The method of claim 17, wherein the patient is diagnosed with UIC when the level of one of the proteins IL-6, IL-8, and GRO in the urine sample from the human patient is higher than the level of the respective protein in the control urine samples.

23. The method of claim 22, wherein the patient is diagnosed with UIC when the level of one of the proteins IL-6, IL-8, and GRO in the urine sample from the human patient is at least 1.5 times greater than the level of the respective protein in the control urine samples.

24. The method of claim 22, wherein the patient is diagnosed with UIC when the levels of two of the proteins IL-6, IL-8, and GRO in the urine sample from the human patient are higher than the levels of the respective proteins in the control urine samples.

25. The method of claim 24, wherein the patient is diagnosed with UIC when the levels of two of the proteins IL-6, IL-8, and GRO in the urine sample from the human patient are at least 1.5 times greater than the levels of the respective proteins in the control urine samples.

26. The method of claim 24, wherein the patient is diagnosed with UIC when the levels of each of the proteins IL-6, IL-8, and GRO in the urine sample from the human patient are higher than the levels for each of the respective proteins in the control urine samples.

27. The method of claim 26, wherein the patient is diagnosed with UIC when the levels of each of the proteins IL-6, IL-8, and GRO in the urine sample from the human patient are at least 1.5 times greater than the levels for each of the respective proteins in the control urine samples.

* * * * *

SEQUENCE LISTING

<160> NUMBER OF SEQ ID NOS: 3

<210> SEQ ID NO 1
<211> LENGTH: 212
<212> TYPE: PRT
<213> ORGANISM: Homo sapiens

<400> SEQUENCE: 1

Met Asn Ser Phe Ser Thr Ser Ala Phe Gly Pro Val Ala Phe Ser Leu
1               5                   10                  15

Gly Leu Leu Leu Val Leu Pro Ala Ala Phe Pro Ala Pro Val Pro Pro
            20                  25                  30

Gly Glu Asp Ser Lys Asp Val Ala Ala Pro His Arg Gln Pro Leu Thr
        35                  40                  45

Ser Ser Glu Arg Ile Asp Lys Gln Ile Arg Tyr Ile Leu Asp Gly Ile
    50                  55                  60

Ser Ala Leu Arg Lys Glu Thr Cys Asn Lys Ser Asn Met Cys Glu Ser
65                  70                  75                  80

Ser Lys Glu Ala Leu Ala Glu Asn Asn Leu Asn Leu Pro Lys Met Ala
                85                  90                  95

Glu Lys Asp Gly Cys Phe Gln Ser Gly Phe Asn Glu Glu Thr Cys Leu
            100                 105                 110

Val Lys Ile Ile Thr Gly Leu Leu Glu Phe Glu Val Tyr Leu Glu Tyr
        115                 120                 125

Leu Gln Asn Arg Phe Glu Ser Ser Glu Glu Gln Ala Arg Ala Val Gln
    130                 135                 140

Met Ser Thr Lys Val Leu Ile Gln Phe Leu Gln Lys Lys Ala Lys Asn
145                 150                 155                 160

Leu Asp Ala Ile Thr Thr Pro Asp Pro Thr Thr Asn Ala Ser Leu Leu
                165                 170                 175

Thr Lys Leu Gln Ala Gln Asn Gln Trp Leu Gln Asp Met Thr Thr His
            180                 185                 190

Leu Ile Leu Arg Ser Phe Lys Glu Phe Leu Gln Ser Ser Leu Arg Ala
        195                 200                 205

Leu Arg Gln Met
        210

<210> SEQ ID NO 2
<211> LENGTH: 99
<212> TYPE: PRT
<213> ORGANISM: Homo sapiens

<400> SEQUENCE: 2

Met Thr Ser Lys Leu Ala Val Ala Leu Leu Ala Ala Phe Leu Ile Ser
1               5                   10                  15

-continued

```
Ala Ala Leu Cys Glu Gly Ala Val Leu Pro Arg Ser Ala Lys Glu Leu
            20                  25                  30

Arg Cys Gln Cys Ile Lys Thr Tyr Ser Lys Pro Phe His Pro Lys Phe
            35                  40                  45

Ile Lys Glu Leu Arg Val Ile Glu Ser Gly Pro His Cys Ala Asn Thr
 50                          55                  60

Glu Ile Ile Val Lys Leu Ser Asp Gly Arg Glu Leu Cys Leu Asp Pro
 65                      70                  75                  80

Lys Glu Asn Trp Val Gln Arg Val Val Glu Lys Phe Leu Lys Arg Ala
                 85                  90                  95

Glu Asn Ser

<210> SEQ ID NO 3
<211> LENGTH: 107
<212> TYPE: PRT
<213> ORGANISM: Homo sapiens

<400> SEQUENCE: 3

Met Ala Arg Ala Ala Leu Ser Ala Ala Pro Ser Asn Pro Arg Leu Leu
 1               5                  10                  15

Arg Val Ala Leu Leu Leu Leu Leu Val Ala Ala Gly Arg Arg Ala
            20                  25                  30

Ala Gly Ala Ser Val Ala Thr Glu Leu Arg Cys Gln Cys Leu Gln Thr
            35                  40                  45

Leu Gln Gly Ile His Pro Lys Asn Ile Gln Ser Val Asn Val Lys Ser
         50                  55                  60

Pro Gly Pro His Cys Ala Gln Thr Glu Val Ile Ala Thr Leu Lys Asn
 65                      70                  75                  80

Gly Arg Lys Ala Cys Leu Asn Pro Ala Ser Pro Ile Val Lys Lys Ile
                 85                  90                  95

Ile Glu Lys Met Leu Asn Ser Asp Lys Ser Asn
             100                 105
```